United States Patent
Vazquez Duhalt et al.

(10) Patent No.: US 10,480,012 B2
(45) Date of Patent: Nov. 19, 2019

(54) CYP-P22 BIOCATALYTIC NANOPARTICLES WITH CYTOCHROME P450 ACTIVITY FOR PRODRUG ACTIVATION

(71) Applicant: UNIVERSIDAD NACIONAL AUTÓNOMA DE MÉXICO, Mexico City (MX)

(72) Inventors: Rafael Vazquez Duhalt, Ensenada (MX); Lorena Paulina Sanchez Sanchez, Mexico City (MX)

(73) Assignee: UNIVERSIDAD NACIONAL AUTONOMA DE MEXICO, Mexico City (MX)

( * ) Notice: Subject to any disclaimer, the term of this patent is extended or adjusted under 35 U.S.C. 154(b) by 106 days.

(21) Appl. No.: 15/577,404

(22) PCT Filed: May 26, 2016

(86) PCT No.: PCT/MX2016/000053
§ 371 (c)(1),
(2) Date: Nov. 28, 2017

(87) PCT Pub. No.: WO2016/195471
PCT Pub. Date: Dec. 8, 2016

(65) Prior Publication Data
US 2018/0327780 A1 Nov. 15, 2018

(30) Foreign Application Priority Data
May 29, 2015 (MX) ............... MX/a/2015/006813

(51) Int. Cl.
| | |
|---|---|
| C12N 15/86 | (2006.01) |
| A61K 47/69 | (2017.01) |
| A61K 9/51 | (2006.01) |
| A61K 38/16 | (2006.01) |
| A61K 38/17 | (2006.01) |
| A61K 38/44 | (2006.01) |
| A61K 45/06 | (2006.01) |
| C07K 14/24 | (2006.01) |
| C07K 14/47 | (2006.01) |
| C07K 14/705 | (2006.01) |
| C12N 9/02 | (2006.01) |

(52) U.S. Cl.
CPC ............... *C12N 15/86* (2013.01); *A61K 9/51* (2013.01); *A61K 38/164* (2013.01); *A61K 38/177* (2013.01); *A61K 38/1732* (2013.01); *A61K 38/44* (2013.01); *A61K 45/06* (2013.01); *A61K 47/6929* (2017.08); *C07K 14/24* (2013.01); *C07K 14/4726* (2013.01); *C07K 14/705* (2013.01); *C12N 9/0081* (2013.01); *C12Y 114/15006* (2013.01)

(58) Field of Classification Search
None
See application file for complete search history.

(56) References Cited

U.S. PATENT DOCUMENTS 5,688,773 A 11/1997 Chiocca et al.

FOREIGN PATENT DOCUMENTS

| | | |
|---|---|---|
| ES | 2253775 T3 | 1/2006 |
| WO | 99/45126 A2 | 9/1999 |

OTHER PUBLICATIONS

An, et al., "Effect of site-directed PEGylation of trichosanthin on its biological activity, immunogenicity, and pharmacokinetics", Biomolecular Engineering, vol. 24, p. 643-649, (2007).
Akhtar, et al., "PEGylation of an osteoclast inhibitory peptide: Suitable candidate for the treatment of osteoporosis", International Journal of Pharmaceutics, vol. 434, p. 429-436, (2012).
Da Silva Freitas, et al., "Chemical and Enzymatic Site Specific PEGylation of hGH", Bioconjugate Chemistry, 2013, vol. 24, p. 456-463.
Cai, et al., "Peptide-Labeled Near-Infrared Quantum Dots for Imaging Tumore Vasculature in Living Subjects", Nano Letters, 2006, vol. 6, No. 4, p. 669-676.
Huang, et al., "Targeted delivery of Chlorotoxin-modified DNA-loaded nanoparticles to glioma via intravenous administration", Biomaterials, vol. 32, p. 2399-2406, (2011).
Hoskins, et al., "Therapeutic Resistance CYP2D6 and tamoxifen: DNA matters in breast cancer", Nature, Aug. 2009, vol. 9, p. 576-586.
C. Kent Osborne, M.D., "Tamoxifen in the Treatment of Breast Cancer", The New England Journal of Medicine, Drug Therapy, vol. 339, No. 22, p. 1609-1618.
Bertrand Rochat, "Role of Cytochrome P450 Activity in the Fate of Anticancer Agents and in Drug Resistance; Focus on Tamoxifen, Paclitaxel and Imatinib Metabolism", Clin. Pharmacokinet, 2005, vol. 44 (4), p. 349-366.
Brauch, et al., "Pharmacogenomics of Tamoxifen Therapy", Clinical Chemistry, vol. 55: No. 10, p. 1770-1782 (2009).
Pirola, et al., "Resveratrol: One Molecule, Many Targets," IUBMB Life, vol. 60(5), p. 323-332, May 2008.
Lin, et al., "An effective sample preparation approach for screening the anticancer compund piceatannol using PHLC coupled with UV and flourescence detection", Journal of Chromatography B, vol. 853, p. 175-182, (2007).
Donato, et al., "Fluorescence-Based Assays for Screening Nine Cytochrome P450 (P450) Activities in Intact Cells Expressing Individual Human P450 Enzymes", Drug Metabolism & Disposition, vol. 32, No. 7, p. 699-706, 2004.
International Search Report for PCT/MX2016/000053 dated Oct. 27, 2016 and English translation (9 pages).
Christopher Paul Wild, "The Role of Cancer Research in Noncommunicable Disease Control", JNCI, vol. 104, Issue 14, Jul. 18, 2012; p. 1051-1058.

(Continued)

*Primary Examiner* — Anand U Desai
(74) *Attorney, Agent, or Firm* — Shumaker, Loop & Kendrick, LLP

(57) ABSTRACT

Hybrid proteins with cytochrome P450 activity and which are encapsulated in a nanocapsid (nanoparticles charged with cytochrome P450 activity) are designed and synthesized, these hybrid proteins being immunologically inert and recognized by breast cancer cells.

17 Claims, 13 Drawing Sheets

Specification includes a Sequence Listing.

(56) References Cited

OTHER PUBLICATIONS

McWhirter, et al. "Chemotherapy induced hepatotoxicity in metastatic colorectal cancer: A review of mechanisms and outcomes," Critical Review in Oncology/Hematology, vol. 88, (2013), p. 404-415.
McFadyen, et al. "Cytochrome P450 enzymes: Novel options for cancer therapeutics", Molecular Cancer Therapeutics, p. 363-371, May 10, 2016.
Huttunen, et al. "Cytochrome P450-Activated Prodrugs: Targeted Drug Delivery", Current Medical Chemistry, 2008 vol. 15, No. 23, p. 2346-2365.
Choudhary, et al. "Comparative expression profiling of 40 mouse cytochrome P450 genes in embryonic and adult tissues," Archives of Biochemistry and Biophysics, vol. 414, (2003), p. 91-100.
Zhao, et al. "Relative imbalances in the expression of catechol-O-methyltransferase and cytochrome P450 in breast cancer tissue and their association with breast carcinoma," Maturitas, vol. 72, (2012), p. 139-145.
Huttunen, et al. "Cytochrome P450-Activated Prodrugs: Targeted Drug Delivery", Current Medicinal Chemistry, (2008), vol. 15, No. 23, p. 2346-2365.
Ravichandran, et al. "Crystal Structure of Hemoprotein Domain of P450BM-3, a Prototype for Microsomal P450's", Science, vol. 261, Aug. 6, 1993, p. 731-736.
Anzenbacherova et al. "Flexibility and stability of the structure of cytochromes P450 3A4 and BM-3", Eur. J. Biocem., vol. 267, p. 2916-2920 (2000) FEBS 2000.
Whitehouse et al. "Evolved CYP102a1 (P450 BM3) variants oxidise a range of non-natural substrates and offer new selectivity options", The Royal Society of Chemistry 2008, p. 966-968.
Di Nardo et al. "Wild-type CYP102A1 as a biocatalyst: turnover of drugs usually metabolised by human liver enzymes", J. Biol Inorg Chem (2007), vol. 12, p. 313-323.
Ai-Lazikani, et al. "Combinatorial drug therapy for cancer in the post-genomic era", Nature Biotechnology, vol. 30, No. 7, Jul. 2012; p. 1-13.
Hecht, et al. "Selection of Cytrochrome P450 Genes for Use in Prodrug Activation-Based Cancer Gene Therapy", Methods in Molecular Medicine, vol. 35: Gene Therapy: Methods and Protocols, p. 77-83.
Xu, et al."Strategies for Enzyme/Prodrug Cancer Therapy", Clinical Cancer Research, vol. 7, p. 3314-3324, Nov. 2001.
Duvaz, et al."Antibody-directed enzyme prodrug therapy (ADEPT): a review", Advanced Drug Delivery Reviews, vol. 26, (1997), p. 151-172.
Francis, et al."A phase I trial of antibody directed enzyme prodrug therapy (ADEPT) in patients with advanced colorectal carcinoma or other CEA producing tumours", British Journal of Cancer (2002), vol. 87, p. 600-607.
Dachs, et al. "From bench to bedside for gene-directed enzyme prodrug therapy of cancer", Anti-Cancer Drugs, vol. 16, No. 4, p. 349-359 (2005).
Cirino, et al. "A self-Sufficient Peroxide-Driven Hydroxylation Biocatalyst", Angew. Chem., 2003, vol. 115, p. 3421-3423.
Sanchez, et al. "Chemotherapy pro-drug activation by biocatalytic virus-like nanoparticles containing cytochrome P450", Enzyme and Microbial Technology, vol. 60, (2014), p. 24-31.
Limon, et al. "Peroxidase activity stabilization of cytochrome P450 BM3 by rational analysis of intromolecular electron transfer", Journal of Inorganic Biochemistry, vol. 122, (2013), p. 18-26, 9 pages.
Lee, et al. "Viruses and Virus-Like Protein Assemblies—Chemically Programmable Nanoscale Building Blocks", Nano Res., (2009), vol. 2, p. 349-364.
Strable, et al. "Current Topics in Microbiology and Immunology", Springer-Verlag Berlin Heidelberg, 2009, vol. 327, 151 pages.
Bamford, et al. "What does structure tell us about virus evolution?" Current Opinion in Structural Biology, 2005, vol. 15, p. 655-663.
Douglas, et al. "Viruses: Making Friends with Old Foes", Science, vol. 312, p. 873-875, May 12, 2016.
Hooker, et al. "Magnetic Resonance Contrast Agents from Viral Capsid Shells: A Comparison of Exterior and Interior Cargo Strategies", 2007, Nano Letters, vol. 7, No. 8, p. 2270-2210.
Ren, et al. "Folic Acid-Conjugated Protein Cages of a Plant Virus: A Novel Delivery Platform for Doxorubicin", Bioconjugate Chem. 2007, vol. 18, p. 836-843.
Verma, et al. "Gene Therapy: Twenty-First Century Medicine", Annu. Rev. Biochem. 2005, vol. 74, p. 711-738.
Lipin, et al. "Encapsulation of DNA and non-viral protein changes the structure of murine polyomavirus virus-like particles", Arch Virol (2008), vol. 153, p. 2027-2039.
Schmidt, et al. "Protein and peptide delivery via engineered polymavirus-like particles", FJ Express Summaries, May 8, 2001, 8 pages.
Abbing, et al. "Efficient Intracellular Devliery of a Protein and a Low Molecular Weight Substance via Recombinant Polyomavirus-like Particles.", The Journal of Biological Chemistry, vol. 279, No. 26, p. 27410-27421, Jun. 25, 2004.
Minten, et al. "Complex Assembly Behaviour During the Encapsulation of Green Flourescent Protein Analogs in Virus Derived Protein Capsules", Macromolecular Bioscience, 2010, vol. 10, p. 539-545.
O'Neil, et al. "Coconfinement of Fluorescent Proteins: Spatially Enforced Communication of GFP and mCherry Encapsulated within the P22 Capsid", Biomacromolecules, 2012, vol. 13, p. 3902-3907.
Iyer, et al. "Exploiting the enhanced permeability and retention effect for tumor targeting", Drug Discovery Today, vol. 11, Nos. 17/18, p. 812-818, Sep. 2006.
Vladimir Torchilin "Tumor delivery of macromolecular drugs based on the EPR effect", Advanced Drug Delivery Review, vol. 63, p. 131-135 (2011).
Teschke, et al. "'Let the phage do the work': Using the phage P22 coat protein structures as a framework to understand its folding and assembly mutants", Virology, vol. 401, p. 119-130 (2010).
Thuman-Commike, et al. "Three-dimensional Structure of Scaffolding-containing Phage P22 Procapsids by Electron Cryo-microscopy", J. Mol. Biol. (1996), vol. 260, p. 85-98.
Chen, et al. "Structural basis for scaffolding-mediated assembly and maturation of a dsDNA virus", PNAS Jan. 25, 2011, vol. 108, No. 4, p. 1355-1360.
Parent, et al. "P22 Coat Protein Structures Reveal a Novel Mechanism for Capsid Maturation: Stability without Auxiliary Proteins or Chemical Crosslinks", Structure, vol. 18, p. 390-401, Mar. 10, 2010.
Fiedler, et al. "RNA-Directed Packaging of Enzymes within Virus-like Particles", Angew. Chem. Int. Ed. 2010, vol. 49, p. 9648-9651.
O'Neil, et al. "Stabilizing viral nano-reactors for nerve-agent degradation", Biomater Sci., 2013, vol. 1, p. 881-886.
Rodriguez, et al. "Minimal "Self" Peptides That Inhibit Phagocytic Clearance and Enhance Delivery of Nanoparticles", Science vol. 339, p. 971-975, Feb. 22, 2013.
Inoue, et al. "Engineering of SV40-based nano-capsules for delivery of heterologous proteins as fusions with the minor capsid proteins VP2/3", Journal of Biotechnology, vol. 134, p. 181-192 (2008).
Kreppel, et al. "Modification of Adenovirus Gene Transfer Vectors With Synthetic Polymers: A Scientific Review and Technical Guide", Molecular Therapy, vol. 16, No. 1, p. 16-29, Jan. 2008.
Comellas-Aragones, et al. "A virus-based single-enzyme nanoreactor", Nature Naotechnology, vol. 2, Oct. 2007; p. 635-639.
Minten, et al. "Catalytic capsids: the art of confinement", Chem. Sci., 2011, vol. 2, p. 358-362.
Patterson, et al. "Nanoreactors by Programmed Enzyme Encapsulation Inside the Capsid of the Bacteriophage P22", ACS Nano, vol. 6, No. 6, p. 5000-5009, 2012.
Patterson, et al. "Virus-like particle nanoreactors: programmed encapsulation of the thermostable CelB glycosidase inside the P22 capsid", Soft Matter, 2012, vol. 8, p. 10158-10166.
Patterson, et al. "Encapsulation of an Enzyme Cascade within the Bacteriophage P22 Virus-Like Particle", ACS Chem. Biol., 2014, vol. 9, p. 359-365.
Glasgow, et al. "Osmolyte-Mediated Encapsulation of Proteins inside MS2 Viral Capsids", ACS Nano, vol. 6, No. 10, p. 8658-8664, 2012.

(56) References Cited

OTHER PUBLICATIONS

Kreppel, et al. "Modification of Adenovirus Gene Transfer Vectors With Synthetic Polymers: A Scientific Review and Technological Guide", Molecular Therapy, vol. 16, No. 1, p. 16-29, Jan. 2008.

Active drug for chemotherapy

Co-expression

| Expression system | CYP/ capsid | CYP Abs$_{280}$ concentration (µM) | CYP CO assay concentration (µM) | CO/ Abs$_{280}$ |
|---|---|---|---|---|
| pETDuet 5h | 156.0 (±0.4) | 123.5 | 9.2 | 0.07 |
| pETDuet O/N | 122.9 (±1.9) | 87.8 | 2.43 | 0.03 |

Differential expression

| Expression system | CYP/ capsid | CYP Abs$_{280}$ concentration (µM) | CYP CO assay concentration (µM) | CO/ Abs$_{280}$ |
|---|---|---|---|---|
| pBAD+pRSF 1 | 129.5 (±0.1) | 135.32 | 31.8 | 0.23 |
| pBAD+pRSF 2 | 109.7 (±2.8) | 123.7 | 42.9 | 0.35 |

FIGURE 8

CYP-P22 BIOCATALYTIC NANOPARTICLES WITH CYTOCHROME P450 ACTIVITY FOR PRODRUG ACTIVATION

REFERENCE TO AN ELECTRONIC SEQUENCE LISTING

The contents of the electronic sequence listing (5309-8US_SeqListing_ST25.txt; Size: 7 KB; and Date of Creation: Jun. 25, 2018) is herein incorporated by reference in its entirety.

TECHNICAL FIELD

The present invention relates to the field of bionanotechnology and nanomedicine to increase cytochrome P450 activity in tumor cells or other tissues for greater efficiency in the activation of prodrugs, helping to contribute to the treatment of cancer, and a better efficiency in the treatment thereof with chemotherapy, or in other treatments where the prodrug is activated by cytochrome P450.

BACKGROUND OF THE INVENTION

Bionanotechnology is a multidisciplinary area of knowledge that combines biological principles with physical and chemical procedures to research and develop nano-level materials with specific functions and new properties. Nanomedicine is the application of bionanotechnology in the field of biomedical sciences and has become a fundamental tool for development of new drug products. One of the biggest challenges in this area is to reduce or eliminate the immune response during nanomaterial supply, as well as to improve its effect by lengthening its bioavailability in the body.

Cancer is a global public health problem that has not yet been resolved affecting health of more than 14 million people annually, 50% of whom die [1]. The most used treatment to fight this important disease is chemotherapy, which in many cases is successful but has dramatic side effects. These side effects can put the patient at risk and can lead to death. Classic drugs used in chemotherapy are mitotic inhibitors, alkylating agents, antimetabolites, topoisomerase inhibitors and anthracenediones (anthracyclines) that inhibit DNA synthesis and mitosis, in order to prevent the rapid proliferation of cells. However, these agents are substances that can exert their toxic activity in healthy cells. Hence the unwanted side effects [2].

Most drugs used in chemotherapy must be activated by P450 cytochromes (CYP) to exert their antitumor activity [3, 4] (Table 1).

TABLE 1

Examples of commercial antitumor prodrugs activated by human CYP (modified from Huttunen et al., 2008 [7]).

| Prodrug | Active drug | Activation mechanism | Human CYP catalyzing the reaction |
| --- | --- | --- | --- |
| Cyclofosfamide | Fosfamide mustard | Hydroxylation | CYP286, CYP2C9, CYP3A4 |
| Ifosfamide | Ifosfamide mustard | Hydroxylation | CYP2B6, CYP3A4 |
| Trofosfamide | Trofosfamide mustard | Hydroxylation | CYP2A6, CYP2B6, CYP2C9, CYP3A4 |
| Pradefovir | PMEA-triphosphate | Hydroxylation | CYP3A4 |
| MB07133 | araC-triphosphate | Hydroxylation | CYP3A4 |
| MB07811 | MB07344 | Hydroxylation | CYP3A4 |
| Buparvaquone hydroxyimine | Buparvaquone | Oxidation | CYP3A4, CYP2B |
| Nabumetone hydroxyimine | Nabumetone | Oxidation | CYP3A4, CYP2A6 |
| DB289 | Furamidine (DB75) | O-demethylation reduction | CYP4F |
| Sibrafiban | Ro 48-3888 | Reduction | — |
| Ximelagratan | Melagartan | Reduction | — |
| Guanoxabenz | Guanabenz | Reduction | — |
| AQ4N | AQ4 | Reduction | CYP3A4, CYP1A1, CYP1A2, CYP2B6 |
| Dacarbazine (DTIC) | MTIC | Hydroxylation | CYP1A1, CYP1A2, CYP2E1 |
| Tegafur | 5-FU | Hydroxylation | CYP2A6, CYP1A2, CYP2C8 |
| 4-ipomeanol | | Oxidation (epoxidation) | CYP1A2, CYP2B7, CYP2C19, CYP2D6, CYP2F1, CYP3A3, CYP3A4, CYP4B1 |
| DDMX (PNU-152243) | PNU-159682 | Cyclation | CYP3A4 |
| Tamoxifen | 4-Hydroxy-tamoxifen | Hydroxylation | CYP2D6 |
| Tamoxifen | N-Demethyl-tamoxifen | N-Demethylation | CYP1A1, CYP1A2, CYP1B1, CYP2C9, CYP2C19, CYP2D6, CYP3A4, CYP3A5 |
| Tamoxifen | Endoxifen | Hydroxylation, N-Demethylation | CYP2D6, CYP3A4 |
| Clopidogrel | R-130964 | Oxidation | CYP3A4, CYP3A5 |

Due to its activity on certain prodrugs (mainly antiviral drugs and chemotherapy drugs) P450 cytochromes (CYPs) are important because is the largest enzymatic complex involved in drug metabolism in our body, playing a key role in metabolism oxidative phase.

CYPs form a large family of microsomal hemoproteins that catalyze many types of oxidation reactions on endogenous and exogenous substrates [7]. Table 1 shows some of the commercially available drugs that are activated by CYPs. There are more than 270 families of different CYPs of which 18 have been identified in mammals. Humans have between 55 and 60 genes that code for CYP, which are expressed mainly in liver and intestines, but may be found in almost all tissues. At cell level they are found in endoplasmic reticulum membranes. In general, CYPs that metabolize endogenous compounds are very specific for certain substrates, while CYPs that metabolize exogenous compounds show a low specificity and are capable of transforming a large variety of compounds [7].

Reactions catalyzed by CYPs are based on monooxygenation, where one atom of the oxygen molecule is incorporated into the substrate. Generally, these enzymes are part of a multienzyme complex since oxygen molecule ($O_2$) activation and the consequent transfer of an oxygen atom to the substrate involves the transfer of electrons from NADPH to CYP, facilitated by other proteins such as cytochrome P450 reductase.

However, the activity of these enzymes in different tissues varies significantly [5], and even more, in some cases, as in breast cancer, CYP activity is much lower in the tumor than in the surrounding healthy cells [6]. This hinders drug supply and dosage, also inducing cytotoxicity in healthy tissues.

On the contrary, CYPBM3 is, for example, a bacterial-origin protein, structurally and functionally similar to human microsomal cytochromes [7b, 7c], with the advantage of being a soluble and stable CYP in aqueous medium, further being able to be produced in large quantities unlike human CYPs. Another interesting feature of this CYP is that it has high plasticity to be subject to both site-directed mutagenesis and directed evolution, to obtain variables capable of transforming a wide variety of non-natural substrates such as alkanes, polyaromatic hydrocarbons and medications [7d; 7e]. These properties make CYPBM3 a versatile enzyme with a series of interesting operational advantages to be used as a model enzyme for encapsulation in viral nanostructures.

Drug Activation Therapy Through Enzymes

Prodrug activation therapy using exogenous enzymes is a proposed strategy to increase efficiency of certain medical procedures, such as chemotherapy. Chemotherapy being one of the most used treatments nowadays to fight cancer [8] shows drastic side effects. One of the objectives of present patent is to increase the local concentration of active drug in tumor cells, which would increase the drug efficiency in the tumor and reduce the toxicity produced by the drug in the rest of the host cells [9]. This strategy is carried out in two steps; firstly, the exogenous enzyme must be directed to the cells of interest and accumulated in the site, then, in a second step, the prodrug (either directed or systemically) is administered, selectively activating in the target cells.

Two methods have been proposed, broadly speaking, to carry out an enzyme supply capable of activating the prodrug, to the cells of interest: gene delivery, known by its acronym in English as GDEPT and active enzyme supply [10].

Gene therapy has been proposed as an alternative to increase CYP activity in tumor cells. GDEPT (gene-directed enzyme prodrug therapy) technique involves introduction to specific tumor cells, of one or several genes that encode for enzymes with the ability to transform prodrugs. These genes can be delivered to tumor cells using different vectors, such as those of viral type [10]. On the other hand, antibody-based therapy, known as ADEPT (antibody-directed enzyme prodrug therapy) has been one of the most developed therapies. The enzyme capable of transforming the prodrug selectively targets target cells, through conjugation with an antibody, which has the ability to specifically bind to antigens that are expressed on tumor cell surface [11]. For both strategies, GDEPT and ADEPT, enzyme-prodrug systems have been developed that have been tested in clinical trials [12,13]; However, there is still no treatment in use based on these therapies to date.

A promising alternative to overcome the problems associated with gene insertion and expression in human (mammalian) cells, is to directly deliver the enzyme to specific targets through virus-like particles (VLPs), Viral Capsids Viral capsids or "virus-like particles" (VLPs) are composed only of viral layer proteins and unlike viruses, do not contain the natural genetic material thereof, so they are not infectious particles. These particles can be used as basic scaffolds for nanostructured material design and manufacture. Within this context, some of the features that make VLPs attractive are the following [17, 18]:

i) highly ordered architectures of nanometric dimensions that have the ability to self-assemble;

ii) about 1031 viruses are estimated to inhabit the Earth [19], there is a great diversity of both sizes (17-1500 nm in icosahedral capsids) within this vast number, as well as in different forms, with icosahedral, filamentous capsids and helical forms being predominant;

iii) monodisperse structures in size and composition, under pH and ionic strength particular conditions;

iv) large surface areas, with a variety of functional groups exposed in a high number of copies, that allow coupling of multiple ligands, either of the same or different molecules. This characteristic makes them polyvalent molecules, with the ability to participate in collectively stronger interactions than their counterparts with unique interaction sites, increasing the binding affinity with the target sites;

v) have cavities that can be used to encapsulate molecules for various purposes;

vi) due to their protein nature they are biocompatible and biodegradable.

Viral nanoparticles have three available interfaces to be either chemically or genetically manipulated: the outer surface, the interface between the protein subunits and the internal surface [20]. The latter surface has been used to encapsulate various materials such as metals [21], drugs [22], DNA [23] and proteins [24] in order to generate new materials, catalysts and delivery systems. Protein encapsulation has focused mainly on the introduction of fluorescent proteins into protein nanostructures. The most widely used model has been green fluorescent protein (GFP) due to its easy detection [25, 26, 27, 28]. However, there are a number of works nowadays where enzymes have been encapsulated inside such containers, generating bionanoreactors with properties and catalytic capacities different from their non-encapsulated counterparts.

Due to its size, pseudo-viral particles cannot be filtered and eliminated by kidney (removal threshold <40 kDa), staying longer circulating in the body (increase of residence time within the body). Moreover, those particles can be modified to modulate their residence time in the bloodstream. Finally and of importance for cancer therapy, particles in the nanometric order (100-500 nm) have been observed that preferentially accumulate within solid tumors due to a phenomenon known as increased permeability and retention effect (EPR effect). This accumulation is due to tumor-promoted blood vessels surrounding said tumor, presenting a disorganized architecture with a series of holes in their structure (200-800 nm), allowing nanoparticle extravasation into the tissue. In addition to that above, particles are retained in these sites due to a deficient lymphatic drainage proper of tumors [29, 30].

For example, P22 bacteriophage is a double-stranded DNA virus that infects *Salmonella typhimurium*. The 58 nm icosahedral nanostructure is composed of some minority proteins (expulsion and portal proteins) and by 420 coat proteins (CP) that are assembled with the help of 60 to 300 scaffold proteins (scaffold protein, SP) in a structure known as procapsid. The P22 procapsid-derived pseudo-viral particle only requires the capsid and scaffolding protein to be assembled. The layer protein consists of 430 amino acids (46.6 kDa) folded into eight distinct domains. In the absence of the scaffold protein, the coat protein is not assembled or, in high concentrations, forms T=4 spheres as well as spiral aberrant structures [31]. The procapsid is made up of 72 capsomeres of the coat protein, twelve of which are forming pentamers and 60 of them hexamers. These hexamers are distorted, with a pore in the center with a diameter ranging from 3 to 4.5 nm [32].

Enzyme Encapsulation Within Viral Capsids

Protein encapsulation within these viral origin vehicles offers a series of advantages to overcome protein limitations as therapeutic agents. First of all, capsids are vehicles with a high load capacity, suitable for transporting considerable protein amounts therein. In addition, the viral nanostructure is capable of conferring protein encapsulated protection against protease degradation [35, 36], as well as a barrier against immune system recognition [37]. Virus immunogenicity can be killed by different methods, such as epitope modification, "self-peptides" [38] and particle coating with polymers such as polyethylene glycol (PEG) [39]. In this way the capsid is chemically modified and not the biopharmaceutical drug in question, thus avoiding negative repercussions on the biological activity of therapeutic protein.

Enzyme encapsulation within pseudo-viral particles has been carried out mainly for the production of bionanoreactors focused on catalysis phenomena study [35, 36, 40, 41, 42, 43, 44], although its use as possible therapeutic agents has also been proposed [37]. The first article reported on enzyme encapsulation in pseudo-viral particles was in 2007, where Cornelias-Aragonés [40] et al., designed a system to study enzyme kinetic behavior at individual level, based on encapsulation of a white horseradish peroxidase in capsids derived from CCMV virus (Cowpea chlorotic mottle virus). After this first work, encapsulation of multiple enzymes (single-variety variants) in different capsids was carried out using different encapsulation strategies (Table 2). High enzyme concentrations, in millimolar amount, reached within viral capsids allowed study of catalysis phenomena in crowded environments simulating those found at cellular level, which would allow a better understanding of such biocatalyst function inside cells.

Despite finding a decrease in activity for most of encapsulated enzymes, new properties in the bionanoreactor are generated for some of these systems, such as a thermostability increase [35, 36], proteolysis resistance [35, 36], protection against the lyophilization process [36], inhibition reversal by substrate [42] and decrease to denaturation under certain operating conditions [40]. For the particular case of cytosine deaminase, which converts the 5-fluorocytosine prodrug to the 5-fluorouracil active drug, the SV40 capsid was used as a vehicle for enzymatic activity supply to CV-1 cells {cell line from monkey kidney), in order to sensitize them to prodrug treatment and induce cell death [37].

Recently, the first article was published where multiple copies of different enzymes were encapsulated in a pseudoviral particle (P22 bacteriophage). The three encapsulated enzymes, CelB glycosidase, ATP-galactosidase and ADP-glycokinase, have the peculiarity of performing a series of cascade reactions in the *Pyrococcus furiosus* sugar metabolism [44]. Contrary to what was expected, no increase in reaction cascade efficiency was found; it is essential to pay special attention to an adequate balance of kinematic parameters of each involved enzyme in order to design an efficient catalytic system. Construction of synthetic metabolomes based on enzyme encapsulation in pseudo-viral particles might generate complex catalytic systems with various practical applications.

Although reports of enzyme or other protein encapsulation within viral capsids to generate bionanoreactors have been disclosed, the use of VLPs as cytochrome enzyme carriers has been poorly addressed, and even with unrepresentative results. Such is the case of the CYP encapsulation in CCMV [15] managing to load up to 14 CYPs per nanoparticle.

TABLE 2

Multiple enzyme encapsulation of the same type in viral capsids

| Enzyme | Capsid | Mconf (nM) | Enzymes per capsid | Kcat/Km regarding Efree | Encapsulation method | Ref |
|---|---|---|---|---|---|---|
| Cytosine deaminase | SV40 | ND | ND | Lower (VNR) | By fusion with capsid internal protein (in vivo) | 37 |
| Peptidase F | Bacteriophage Qβ | ND | 2-18 | Lower 3X (9 enzymes) | By fusion with RNA (in vivo) | 35 |
| Luciferase | Bacteriophage Qβ | ND | 4-8 | Lower 30X (4 enzymes) | By fusion with RNA (in vivo) | 35 |
| Antarctic lipase B pseudozyme | CCMV | 1 | 1.3-4 | Higher (kcat) | By fusion with coiled-coil motif (in vitro) | 41 |
| Alkaline phosphatase | Bacteriophage MS2 | 0.5 | 3.2 (monomers) | Equivalent | By electrostatic interactions. Fusion with negative peptide (in vitro) | 45 |
| Alcohol dehydrogenase | Bacteriophage P22 | 7.2 | 249 ± 13 | Lower 1.6X | By fusion with scaffold protein (in vivo) | 42 |
| CelB glycosidase | Bacteriophage P22 | 2.4 | 87 ± 3.5 (monomers) | Equivalent | By fusion with scaffold protein (in vivo) | 43 |
| Phosphotriesterase | Bacteriophage P22 | 1.1 | 40 ± 10 (monomers) | Lower 600X | By fusion with scaffold protein (in vivo) | 36 |
| P450 Cytochrome | CCMV | 4.9 | 31 | Lower 10X | By electrostatic interactions | 15 |

Mconf: Confinement molarity (enzyme concentration inside the capsid).
ND: Not determined.
VNR: Non-reported value.

Handling of CYPs is not trivial, besides the encapsulation described in the present invention requires the design of a strategy that included the use of a virus scaffold protein to make a fusion protein with CYP, which is not apparent even for someone with technical knowledge in the art.

CYP encapsulation offers many advantages such as those set forth in the present invention. CYPs are very unstable enzymes that lose easily their activity and are difficult to keep in active form. They are usually produced in microsomes (lipid vesicles) and cannot be stored. Being in the viral capsids, CYPs remain stable and can be used, which is very difficult with the isolated protein.

Reduction of Nanoparticle Immunogenicity

Polyethylene glycol (PEG) is an amphipathic polymer commonly used in drug supply and its basic structure is H—(O—CH2-CH2)n-OH. It is a non-immunogenic neutral molecule that can be synthesized in different lengths and has been approved by the North American Food and Drug Administration (FDA) for its use in cosmetics, foods and medicaments. There are numerous publications reporting PEG covalent binding on molecules, significantly reducing its antigenicity and immunogenicity, as well as increasing its solubility, maintaining its in vivo bioactivity [46]. Further, PEG is able to protect peptides, proteins or enzymes from degradation, increasing their survival in the body.

An example of protein immunogenicity reduction by PEG modification is trichosanthin (TCS), a protein that interacts with the type I ribosome used for AIDS and tumor treatment. Its application is limited by a very high immunogenic reaction and its residence time under bloodstream. Pegylated trichosantin has been shown to be 3 to 4 times less immunogenic and to have a non-specific toxicity 0.5 to 0.8 times lower, as well as 4.5 to 5 times longer residence time [47]. The only reported disadvantage is an activity reduction, but by having a longer in vivo circulation time, this activity reduction is compensated.

Likewise, TRAF6 protein (TNF receptor associated factor 6) is an intracellular adapter protein in the osteoclast signaling pathway. TRAF6 inhibitor peptide (SEQ ID NO. 1. DRQIKIWFQNRRMKWK) may hinder this pathway, thus avoiding excessive osteoclastic activity, but as a therapeutic agent of osteoporosis shows several limitations due to its short half-life, rapid kidney elimination, and especially its immunogenicity. However, [48] they were able to significantly improve the properties of this peptide through pegylation with a better bioavailability in laboratory animal plasma and with better incorporation at action site. Therefore, a better therapeutic agent for treatment of osteoporosis was obtained.

Finally, the recombinant human growth hormone (hGH), used in treatment of short size disorders in children and adults was modified in a specific-site way by da Silva Freitas et al. [49], showing that the two tested pegylations retained the native hGH secondary structure and also had a residence time 4.5 times higher and therefore a better systematic exposure in rat pharmacokinetics.

Functionalization and Targeting to Tumor Cells

Targeting of nanoparticles to specific tissues is studied by many research groups around the world. The process called in English "drug delivery" is a research field with promising future in medicine and pharmacology. An example of success in nanoparticle targeting to cancer cells was reported by Cai et al. [50]. Quantum dots were functionalized with a peptide (arginine-glycine-aspartic acid) to target and visualize tumor vascularization. These nanoparticles were administered intravenously in mice carrying human subcutaneous glioblastomas. Tumor luminescence showed good specificity, intensity and contrast. Subsequently, a pegylation gave better stability to quantum points. Another example is the intravenously directed delivery of DNA fragments to gliomas for gene therapy purposes [51]. This group used a highly branched dendrimer (PAMAM) on the nanoscale that was conjugated to chlorotoxin, a polypeptide that binds specifically to receptors expressed in gliomas. In this way, they were able to direct the DNA-containing nanoparticles and specifically bind to nervous system tumor cells.

In the present invention, unlike the state of the art which leads a drug in a targeted and controlled manner to a tissue or tumor in a mammalian or human patient, it is intended to bring the cytochrome P450 (cytochrome P450 enzymatic activity) to the tissue of interest with the aim of activating prodrugs in selected target cells or tissues of a mammalian or human patient; for example, that cytochrome P450 exerts its enzymatic activity in tumor cells, tumor tissues, or other tissues of interest for greater efficiency in prodrug activation, helping to contribute to cancer treatment, with a better efficiency in treatment thereof with chemotherapy in a human patient suffering from a tumor or cancer selected from breast cancer or colon cancer, or in other treatments where the prodrug is activated by cytochrome P450.

Most drugs used in chemotherapy are administered as prodrugs to a mammal or human patient. That is, they are administered in a chemical form that has no biological activity. These compounds are activated once they are ingested or injected into the body. Activation is an enzymatic or catalytic transformation mediated by cytochromes P450 that are found in different tissues.

Tamoxifen is the most widely used drug within prodrugs for treatment of hormone-dependent breast cancer [52]. Tamoxifen acts as a selective modulator of estrogen receptor, inhibiting proliferation of tumor cells [53]. This anti-cancer agent is metabolised by different CYP450 in the body, mainly CYP2D6 and CYP3A4, to give rise to 4-hydroxy tamoxifen and endoxifen active drugs, as well as to a number of clinically inactive metabolites [54, 55]. The active product is a very potent cytotoxic agent, so its dosage and treatment duration must be strictly controlled. The possibility of taking directly and exclusively tamoxifen to tumor cells means that necessary doses are significantly reduced, also reducing drastic side effects and increasing treatment effectiveness. On the other hand, resveratrol is a polyphenolic compound naturally produced in plants. In addition to its role as phytoalexin (antimicrobial and antioxidant activities), a series of anti-inflammatory, cardioprotective and anticancer properties have been attributed, both to prevent and treat tumor development [56]. It has been found that a hydroxylated resveratrol derivative, piceatannol, has the ability to function as a more potent chemotherapeutic agent than resveratrol among many other biological activities [57]. This compound is able to suppress cancer cell proliferation and induce apoptosis These properties make piceatannol an interesting potential drug in cancer treatment.

SUMMARY OF THE INVENTION

The present invention relates to a therapeutic strategy based on nanotechnology that carries cytochrome P450 (cytochrome P450 enzymatic activity) to tumor cells, tumor tissues or other tissues of interest with the aim of activating the prodrugs (greater efficiency in prodrug activation) in said selected mammalian or human patient tissues; for example, that cytochrome P450 exerts its enzymatic activity on tumor cells, tumor tissues, or other tissues of interest, contributing for example, in chemotherapy treatment of cancer in a human patient suffering from a tumor or cancer, selected from breast cancer or colon cancer, or in other treatments where the prodrug is activated by cytochrome P450 achieving a better treatment efficiency, a decrease in required medication doses and a decrease in side effects. Thus, local concentration of active drug in tumor cells or other tissues is increased, increasing drug efficiency in the tumor or tissue and reducing the toxicity produced by the drug in the rest of the host cells.

Thus, the present invention deals with an increase of CYP activity in tumors or tumor mass, or other tissues by means of nanoparticles loaded with cytochrome P450 activity (CYP-P22) containing this biocatalytic activity and that are recognized by tumor cells, tumor mass or tissues where the prodrug is activated by cytochrome P450.

In a particular embodiment of the invention, a method for obtaining nanoparticles loaded with non-immunogenic cytochrome P450 (CYP-P22) activity with CYP activity for prodrug activation in general and particularly anticancer agents is presented, and which are recognized by tumor cells or tissues of a mammal or human patient, wherein the prodrug is activated by cytochrome P450.

Loaded, immunologically inert nanoparticles (CYP-P22), with cytochrome P450 activity and capable of being recognized by tumor tissues, tumor mass, or other tissues are used to increase prodrug activation specifically in the tissue of interest or tissue where the prodrug is activated by cytochrome P450 and thus diminish the toxic effects in healthy tissues.

BRIEF DESCRIPTION OF THE FIGURES

FIG. 2A: pET 15 h; 2B: pBAD+pRSF 1; 2C: pET 5 h; 2D: pBAD+pRSF 2.

FIG. 8. Number of enzymes per capsid and proportion of active CYP for each expression system: co-expression and differential expression.

DETAILED DESCRIPTION OF THE INVENTION

Figure 1:
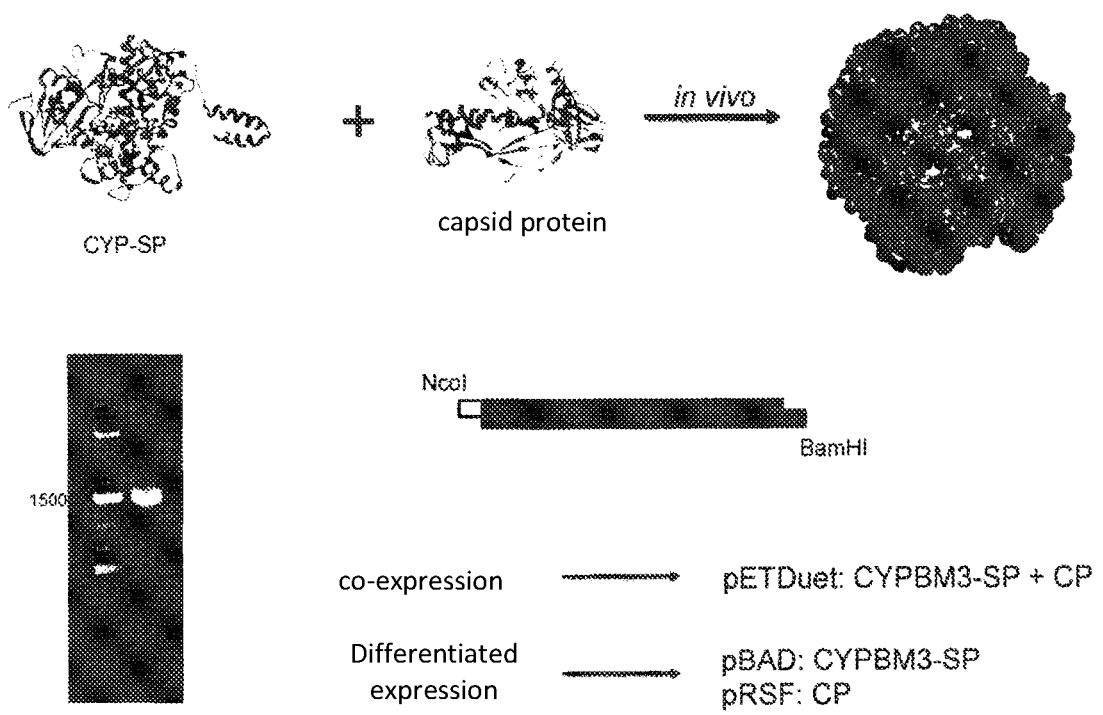
FIG. 1. General procedure scheme of cloning, expression and in vivo encapsulation of $CYP_{BM3}$ in bacteriophage P22 capsids.
Figure 2:
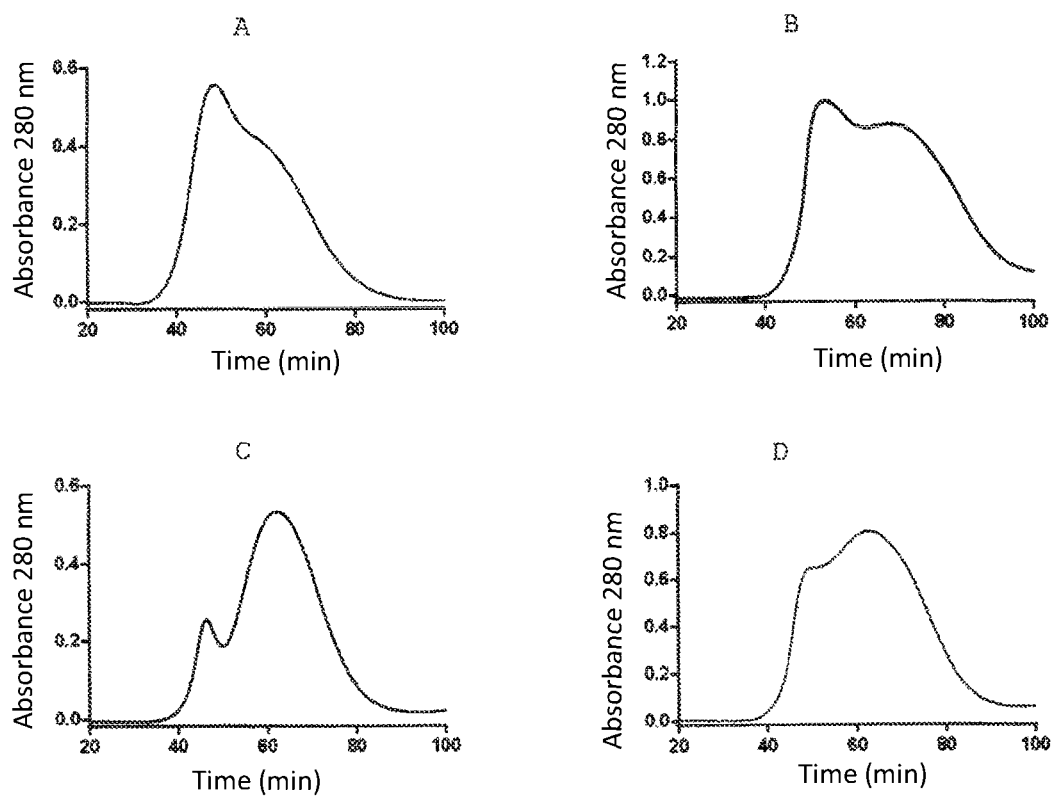
FIGS. 2A-2D. Analysis of P22-CYP nanostructure formation by gel filtration chromatography. The correctly assembled structures elute around 65 min; the aberrant structures elute around 45 min. Protein elution was monitored at λ=280 nm.

Terminology used in present invention is intended to describe particular embodiments and is not intended to be limiting of the invention. As used herein, CYP-P22 or CYP-P22 biocatalytic nanoparticle refers to a nanoparticle, nanostructure or biocatalytic nanocapsid loaded with cytochrome P450 activity (nanoparticles or nanostructures or nanocapsids containing cytochrome P450). More particularly, CYP-P22 is a cytochrome P450 encapsulated in a bacteriophage P22 nanocapsid.

The term CYP-P22 should also be understood in its inverse form P22-CYP, both referring to CYP-P22 nanoparticle, the nanoparticle loaded with cytochrome P450.

In turn, CYP-P22 (containing the cytochrome P450 nanoparticle or nanostructure) has enzymatic activity on prodrugs, such as, for example, prodrugs selected from: anticancer agents (Tamoxifen, Tegafur, Ifosfamide, Resveratrol, and the like), antithrombotic agents (e.g., Clopidogrel and the like), analgesics (such as nabumetone, and the like), antiparasitic agents (such as Pafuramidine and the like), antihistaminics (such as Loratadine, and the like), and others; and said CYP-P22 is immunologically inert and capable of being recognized by tumor cells, tumor tissues or other tissues of interest. Furthermore, prodrugs will be activated in a target cell or tissue of interest. Thus, in the present invention the CYP enzymatic activity is carried to the tissue or target cell that will activate the prodrugs in said targets selected from a mammalian or human patient suffering from a tumor mass or cancer selected from breast cancer or colon cancer or for other treatments, where the prodrug is activated by cytochrome P450, achieving a better treatment efficiency, a decrease in required medication doses and a decrease in side effects. Thus, the local concentration of active drug in tumor cells, tumor tissues or other tissues is increased, increasing drug efficiency in the tumor or tissue and reducing toxicity produced by the drug in the rest of the host cells.

The invention consists of nanoparticles loaded with cytochrome P450 (enzymes of the cytochrome P450 group encapsulated within nanoparticles), where a CYP-SP protein is located inside a P22 nanocapsid. These biocatalytic nanoparticles are functionalized to be recognized by tumor cells, tumor tissues or other tissues in a treatment wherein the prodrug is activated by cytochrome P450, and are immunologically inert, and catalytically active. The present invention consists in cytochrome P450 molecule encapsulation within viral capsids. Enzymatic nanoparticles or nanoparticles loaded with cytochrome P450 activity will be coated with bifunctional dendritic polyethylene glycol and finally functionalized with some cyclic peptide or other specific ligand to be recognized by tumor cells or other tissues of interest of a mammal or human being. CYP-P22 biocatalytic nanoparticles are capable of transforming prodrugs used in chemotherapy or in other therapies, including treatments requiring cytochrome P450 enzymatic activity on selected prodrugs such as: anticancer agents (Tamoxifen, Tegafur, Ifosphamide, Resveratrol, and the like), antithrombotic agents (e.g., Clopidogrel and the like), analgesics (such as nabumetone, and the like), antiparasitic agents (such as Pafuramidine and the like), antihistaminics (such as Loratadine, and the like), and others. Due to their coating nature, biocatalytic nanoparticles are immunologically inert and are recognized by receptors located on the surface of tumor cells or cells of other tissues of interest. Nanoparticles containing cytochrome P450 (CYP-P22) increase enzymatic activity on the surface of the tumor tissues, tissues with a tumor mass or tissues of interest where prodrugs are activated more efficiently and at the required site, such as, for example, prodrugs used in chemotherapy or other therapies and are selected from antithrombotic, analgesic, antiparasitic, antihistaminic agents, and any other therapy or treatment wherein a prodrug is activated by P450.

The method to produce or synthesize these CYP-P22 biocatalytic and immunologically inert vehicles (nanoparticles loaded with cytochrome P450 activity), that activate prodrugs in a target cell, for example to increase CYP activity in tumors or other tissues of interest and in a treatment wherein the prodrug is activated by cytochrome P450, includes the following procedure:

A) Cloning of CYP gene is performed in the pETDuet+ SP+CP P22 vector. For this end, oligonucleotides are designed to amplify the gene encoding for CYP with insertion of specific restriction sites, to allow subsequent gene ligation in pETDuet vector.

B) Ligation is carried out between the PCR product encoding for CYP gene and the linearized vector pETDuet+ SP+CP P22 and the cytochrome gene fused to scaffolding protein gene (CYP-SP) is obtained. Ligation is used to transform electrocompetent cells. The presence of the insert is checked by inoculating transformed cells in LB boxes with the specific selection antibiotic. The plasmid is purified by alkaline lysis and plasmids will be sequenced to verify the correct inclusion of CYP gene into pETDuet vector in phase with the scaffold protein that results in plasmid pETDuet CYP-SP+CP P22.

C) Plasmid CYPBM3-SP and CP P22 is expressed. Plasmid pETDuet CYP-SP+CP P22 is transformed into electrocompetent BL21 cells. At the end of recovery, cells are cultured in boxes with the selection antibiotic and are grown. Induction of transformed strain is carried out in antibiotic cultures (for selection), the inducer and the aminolevulinic acid as a precursor in heme synthesis.

D) P22 capsids containing cytochrome P450 are purified by supernatant ultracentrifugation from cell lysis. Subsequently the sample is subjected to gel filtration and the corresponding fractions to the elution of the correctly assembled capsids are collected and then concentrated by means of ultracentrifugation. The capsid pellet is resuspended and its structure is analyzed by transmission electron microscopy (TEM).

E) Subsequently catalytic nanoparticle pegylation is performed. Modification with polyethylene glycol of viral capsid surface is carried out with bi-functional polyethylene glycol. In this stage, the safety of nanoparticles can be evaluated on activation of different lymphoid cell subpopulations. Likewise, nanoparticle toxicity is measured on these same linfoid cells.

F) Nanoparticles loaded with cytochrome P450 activity are functionalized for targeting tumor cells such as breast tumor cells, or other tissues of interest, with some cyclic peptide or other ligand related to receptors that are present in tumor cells, tumor tissues or other tissues.

G) Determination of enzymatic activity of loaded biocatalytic nanoparticles is carried out, for example by means of the transformation of Tamoxifen or another prodrug selected from: tamoxifen, resveratrol, tegafur, ifosfamide, clopidogrel, nabumetone, pafuramidine, loratadine. Reactions will be initiated by adding $H_2O_2$ 5 mM or glucose oxidase+glucose and reaction progress is monitored by HPLC equipped with a C18 reverse phase column.

H) Evaluation of affinity of the nanoparticles loaded with cytochrome P450 activity functionalized in tumor cells in vitro can be carried out for example in human MCF7 breast cancer cells maintained in DMEM medium (Dulbecco's Modified Eagle's Medium) supplemented with 10% fetal bovine serum. Cells are cultured at 37° C. in 5% $CO_2$ and with nanoparticles before treatment, the cells are washed twice with serum-free medium and then 1 mL of serum-free medium will be added. Subsequently, the functionalized loaded nanoparticles are added to each well and incubated for 4 hours. After incubation, the supernatant is removed and 1 mL of fresh medium containing 10% fetal bovine serum is incubated for further 48 hours.

I) The presence of biocatalytic nanoparticles (loaded nanoparticles) with CYP activity is evaluated in transformation of 7-benzyloxy-4-trifluorometyl-coumarin (BFC) monitored by fluorescence according to the method of Donato et al. [58]. The fluorescence assay for determining CYP activity is performed with a direct incubation of cultured tumor cells in a 12-well plate in the presence of BFC 100 µM. BFC is added dissolved in acetonitrile, ensuring that final acetonitrile concentration in the wells does not exceed 0.5% (v/v). After 60 min incubation at 37° C. the incubation medium is removed and the conjugated products of CYP transformation will be hydrolyzed with a mixture of 3-giucoronidase/arylsulfatase for 2 hours at 37° C. Finally, samples are diluted with the corresponding solution and product fluorescence (7-hydroxy-4-trifluoromethylcoumarin, HFC) is quantified in a spectrofluorimeter with 410 nm excitation and 510 nm emission.

J) CYP-P22 or biocatalytic nanoparticle efficiency in prodrug activation is determined by determining the tumor cell viability previously treated with nanoparticles in the presence of the prodrug or in combination with the prodrug selected from: tamoxifen, resveratrol, tegafur, ifosfamide, clopidogrel, nabumetone, pafuramidine, loratadine.

The embodiments of the invention will become apparent from the following examples, since CYP-P22 specifically carry to tumor cells, tumor tissues or other tissues the cytochrome P450 activity that activates prodrugs used in chemotherapy more efficiently and at the required site, or in other treatments where the prodrug is activated by cytochrome P450, without limiting the scope to some type of cancer or condition; such as, a cancer selected from breast or colon cancer.

EXAMPLES

Example 1. CYP Expression and Encapsulation

A) Cloning of CYP gene is carried out in pETDuet+SP+ CP P22 vector. For such end, oligonucleotides (SEQ ID NO:

2 and 3) are designed to amplify the gene coding for CYP with insertion of specific restriction sites, NcoI and BamHI, to allow subsequent gene ligation in pETDuet vector (FIG. 1).

```
CYPNcolfw
                                          SEQ. ID. NO. 2
5'AAAAATCATGCCATGGCAATTAAAGAAATGCCT3'

CYPBamHIReverse
                                          SEQ. ID. NO. 3
5'AAAAAAGCGGGATCCAGTGCTAGGTGAAGGAA3'
```

Figure 12:
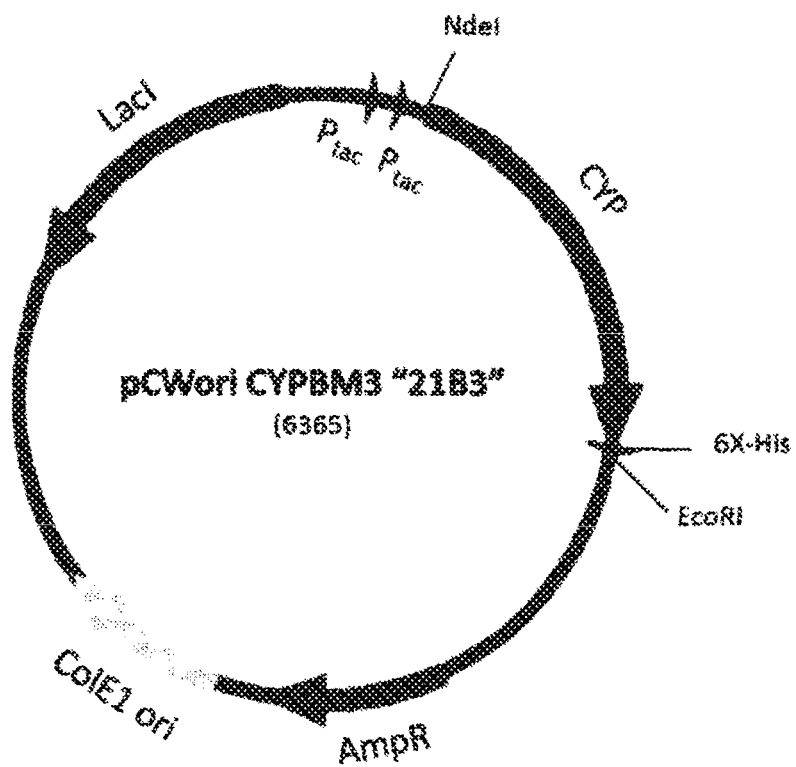
FIG. 12. Plasmid pCWori CYPBM3 "21B3"
Figure 13:
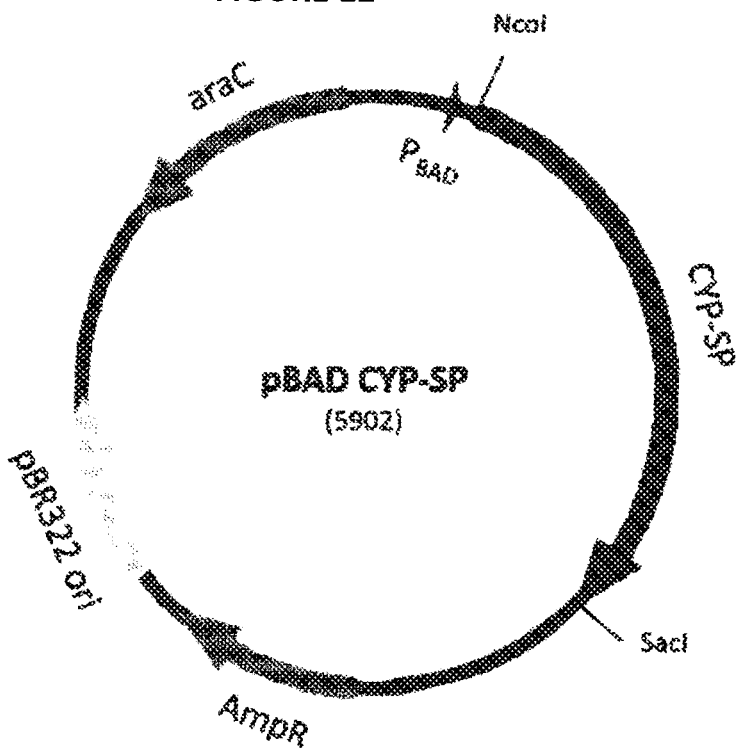
FIG. 13. Plasmid pBAD CYP-SP
Figure 14:
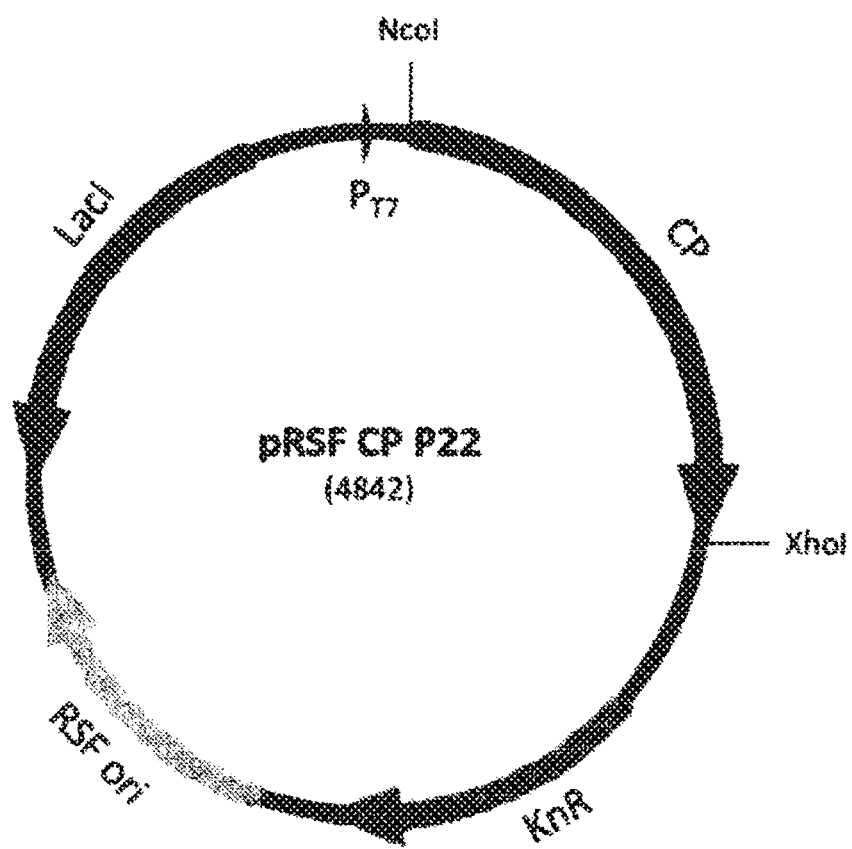
FIG. 14. Plasmid pRSF CP P22

A PCR reaction is carried out using the plasmid pCWori CYPBM3 (ampicillin resistance, double ptac promoter, IPTG inducible, gene coding for heme domain of CYPBM3 "21B3" mutant) (FIG. 12), 10 picomoles of each oligo and Pfu Ultra DNA polymerase. Gene amplification (~1400 bp) is checked by means of a 1% agarose gel electrophoresis using TAE as a run buffer. A voltage of 100 V is used for 25 min. PCR reaction is digested with 1 µl of DpnI for 2 h at 37° C. to remove the parental plasmid. The reaction is then cleaned and DNA is resuspended in 40 uL of mQ grade water. PCR product is digested with 40 units of NcoI and BamHI restriction enzymes). Total reaction volume is brought to 50 uL and incubated at 37° C. for 16 h, the pETDuet plasmid containing the scaffold protein fragment gene, SP141-303, and the bacteriophage P22 coat protein is digested in the same way as the PCR product explained above. Digestion is run on a 1% agarose gel in TAE buffer. The band corresponding to the linearized vector is cut and DNA is extracted from agarose gel.

Figure 9:
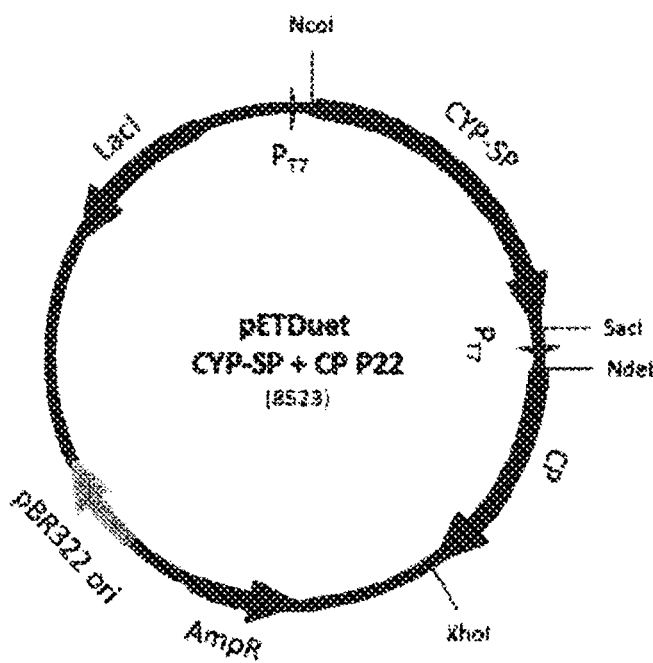
FIG. 9. Plasmid pETDuet CYP-SP+CP P22.

B) Ligation is performed between the PCR product coding for the CYP gene and the pETDuet+SP+CP P22 linearized vector using the T4-DNA ligase enzyme incubating at room temperature for 6 h. 1 µl of ligation was taken to transform 25 µl of electrocompetent 10 G cells. 250 µl of transformed cells were plated in a LB box with ampicillin and allowed growing for 16 h at 37° C. The presence of insert was verified (CYPBM3 gene) for 16 colonies by a colony PCR reaction with CYPNcolfw and CYPBamHIReverse oligonucleotides. Thus, cytochrome gene fused to the scaffold protein gene is obtained, while ligation is used to transform electrocompetent cells. The plasmid is purified by alkaline lysis and plasmids will be sequenced to check the correct incorporation of CYP gene into pETDuet vector in phase with the scaffold protein that results in pETDuet CYP-SP+CP P22 plasmid {FIG. 9}, which comprises a gene encoding CYPBM3 "21B3" fused to SP, a P22 scaffold protein fragment, plus the P22 bacteriophage coat protein gene.

SEQ. ID. NO. 4 corresponds to CYPBM3 "2163" amino acid sequence fused to P22 bacteriophage scaffold protein:

```
MAIKEMPQPKTFGELKNLPLLNTDKPVQALMKIADELGEIFKFEAPGRVT

RYLSSQRLVKEACDESRFDKNLSQALKFVRDFAGDGLATSWTHEKNWKKA

RNILLPSLSQQAMKGYHAMMVDIAVQLVQKWERLNSDEKIEVPEDVTRLT

LDTIGLCGFNYRFNSFYRDQPHPFITSMVRALDEAMNKLQRANPDDPAYD

ENKRQFQEDIKVMDLVDKIIADRKASGEQSDDLLTHMLHGKDPETGEPLD

DENIRYQIITFLIAGHETTSGLLTFALYFLVKNPHVLQKAAEEAARVLVD

PVPSYKQVKQLKYVGMVLNEALRLWPTAPAFSLYAKEDTVLGGEYPLEKG

DELMVLIPQLHRDKTIWGDDVEEFRPERFENPSAIPQHAFKPFGNGQRAC

IGQQFALHEATLVLGMMLKHFDFEDHTNYELDIEETLTLKPEGFVIKAKS

KKIPLGGIPSPSTGSLVPRGSCRSNAVAEQGRKTQEFTQQSAQYVEAARK

HYDAAEKLNIPDYQEKEDAFMQLVPPAVGADIMRLFPEKSAALMYHLGAN

PEKARQLLAMDGQSALIELTRLSERLTLKPRGKQISSAPHADQPITGDVS

AANKDAIRKQMDAAASKGDVETYRKLKAKLKGIR
```

C) CYPBM3-SP and CP P22 plasmid is expressed. pET-Duet CYP-SP+CP P22 plasmid is transformed into electrocompetent BL21 cells. At the end of the recovery, the cells are cultured at least 1 h in LB boxes with the selection antibiotic, ampicillin and grown for 16 h at 37° C.

Induction of the transformed strain is carried out in cultures with the antibiotic (for selection), the inducer and aminolevulinic acid as a precursor in the heme synthesis.

CYPBM3-SP and CP P22 Simultaneous Expression (Co-Expression)

Two induction schemes were followed. For the first scheme, 2 mL of a transformed strain pre-culture was taken to inoculate a 250 mL culture of TB medium with Amp added with 0.5 m of Thiamine and trace elements. It was allowed to grow at 37° C. at 180 rpm until reaching $OD_{600}$=0.8. At this point, it was induced with IPTG 0.5 mM and aminolevulinic acid 1 mM was added. The culture was allowed to grow for additional 5 h at 30° C. at 135 rpm. For the second scheme, 2 mL of a transformed strain pre-culture was taken to inoculate a 250 mL culture of TB medium with Amp added with Thiamine 0.5 mM and trace elements. It was allowed to grow at 37° C. for 7 h at 150 rpm. At this point, it was induced with IPTG 0.5 nM and aminolevulinic acid 1 mM was added. The culture was allowed to grow for additional 15 h at 30° C. at 135 rpm. At the end of the induction, the cultures were centrifuged cold at 3840×g for 10 min, cells were resuspended in lysis buffer (Na2HPO4 50 mM, NaCl 100 mM, pH 7.6) and the sample was sonicated. It was centrifuged at 12,000×g for 30 min at 4° C. and the supernatant was recovered. {FIG. 8}

CYPBM3-SP and CP P22 Differential Expression

Cloning of CYPBM3-SP Gene into pBAD Vector

To clone the cytochrome gene fused to the scaffold protein gene (CYP-SP) in pBAD vector, pETDuet CYP-SP-CP P22 plasmid was digested with 30 units of NcoI and SacI restriction enzymes at 37° C. for 3 h. The reaction was cleaned using MinElute Reaction Cleanup Kit and DNA was resuspended in 30 µl of mQ grade water. Subsequently the sample was incubated with 2.5 units of Antarctic phosphatase for 16 h at 37° C. in a final volume of 30 uL in order to dephosphonate pETDuet vector still present in the mixture thus avoiding its recirculation. Enzyme inactivation at 65° C. for 30 min was carried out.

pBAD plasmid was also digested with 30 units of NcoI and SacI restriction enzymes at 37° C. for 3 h. Digestion was run on a 1% agarose gel in TAE buffer. The band corresponding to the linearized vector was cut and DNA extraction of agarose gel was done using the QIAquick gel extraction kit.

Then ligation between the CYP-SP gene and the linearized vector pBAD was carried out using the 4-DNA ligase enzyme, incubating at room temperature for 6 h. 1 µL of ligation was taken to transform 25 µL of electrocompetent 10G cells. 250 µl of transformed cells were plated in a LB box with ampicillin and allowed to grow for 16 h at 37° C. The presence of a CYP-SP construct for 8 colonies was verified by a colony PCR reaction with CYPNcolfw and CYPBamHIReverse oligonucleotides, following the same previously reported PCR program. Finally, 2 clones were randomly grown (with a previously verified insert) to purify plasmid by alkaline lysis using Qiagen solutions and columns (QIAprep Spin Miniprep kit).

The correct incorporation of CYP-SP gene into pBAD vector was verified, resulting in plasmid pBAD CYP-SP.

Plasmids pBAD CYP-SP (ampicillin resistance, araBAD promoter, arabinose-inducible, gene coding for CYPBM3 "21B3" fused to SP141-303, a protein fragment of P22 scaffold) and pRSF CP P22 (kanamycin resistance, T7 promoter, IPTG inducible, gene encoding the bacteriophage P22 coat protein) (30 ng each) in 25 µL of BL21 competent cells. At the end of 1 hour of recovery, 20 cells were plated in LB boxes with ampicillin and kanamycin and were grown for 16 h at 37° C. CYP-SP protein was firstly expressed to subsequently express the CP coat protein. Two schemes with different inducer concentrations were followed. 1 L of culture was carried out distributed in 4 flasks with 250 mL each. 2.5 mL of a transformed strain preculture was taken to inoculate each 250 mL culture of TB medium with Amp and Km added with Thiamine 0.5 mM and trace elements. It was allowed to grow at 35° C. at 150 rpm for 7 h. At this point CYP-SF expression with 0.2% L-arabinose was induced and aminolevulinic acid 1 mM was added. Cultures were allowed to grow for 16 h more at 30° C. at 120 rpm. Subsequently, CP expression was induced by adding 0.5 mM of IPTG and cultures were grown for 3 h more at 30° C. and 150 rpm. For the second induction scheme, differential expression was performed as explained above, but 0.125% L-arabinose and 0.3 Mm IPTG were used to induce cultures. At the end of induction cultures were centrifuged cold at 3840×g for 10 min, cells were resuspended in lysis buffer (50 mM Na2HPO4, 100 mM NaCl, pH 7.6) and the sample was sonicated. Centrifuged at 12,000×g for 30 min at 4° C. and the supernatant was recovered (FIG. 8)

Example 2. CYP-VLPs Purification and Characterization

D) At the end of induction, cultures were centrifuged cold at 4000×g for 10 min, cells were resuspended in lysis buffer and the sample was sonicated. It was centrifuged at 12,000×g for 30 min at 4° C. and the supernatant was recovered. P22 capsids containing (encapsulating) cytochrome P450 (CYP-P22) are purified by supernatant ultracentrifugation from cell lysis using a 35% sucrose cushion.

CYP-SP Amount and Concentration Per P22 Capsid

The number of enzymes per capsid was calculated using the following equation:

$$CYP, SP_{per\ capsid} = \frac{M_{caspid+CYP,SP} - M_{capsid}}{M_{CYP,SP}}$$

where $M_{capsid-CYP.SP}$=Absolute capsid mass with encapsulated enzyme (experimentally determined value by HPLC-MALS-RI). $M_{capsid}$=46.6 kDa×420 subunits=19572 kDa. MCYP. SP=71.5 kDa (theoretically calculated with Serial Cloner 2.6 program, Franck Pérez, SerialBasics).

Using the number of enzymes per capsid, the CYP-SP concentration in the sample was calculated as follows:

$$A_T = A_{CP} + A_{CYP.SP}$$

where AT is the total sample absorbance at 280 nm, ACP is the absorbance contribution of the coat protein and ACYP-SP is the absorbance contribution of CYPBM3 fused to the scaffolding protein. To measure the total sample absorbance, a P22-CYP aliquot encapsulated in PBS buffer was denatured with 6M guanidine chloride and β-mercaptoethanol 1 mM, the Abs280 was recorded after 5 min of incubation. Above equation can be rewritten according to the Lambert-Beer Law as:

$$A_T = C_{CP}\varepsilon_{CP}l + C_{CYP.SP}\varepsilon_{CYP.SP}l$$

where CCP and CCYP.SP are protein concentrations for CP and CYP-SP respectively; ε refers to the extinction coefficients for each protein, $\varepsilon_{280}$ CP-44920 $M^{-1}$ $cm^{-1}$ and $\varepsilon_{280}$ CYP.SP-52830 $M^{-1}$ $cm^{-1}$ (theoretically calculated with the ProtParam program, Gasteiger, 2005), and is the distance traveled by light through the cell (in this case=1 cm).

The equation was then put in terms of a single variable, CCYP-SP, using the relationship between the CP number and the CYP-SP number per capsid. Example (assuming that 109.7 CYP-SP per capsid was encapsulated):

$$420CP{:}109.7CYP\text{-}SP\ 420/109.7{=}3.8$$

$$C_{CP}=3.8(C_{CYP.SP})$$

$$A_T=3.8C_{CYP.SP}\varepsilon_{CP}l+C_{CYP.SP}\varepsilon_{CYP.SP}l$$

Finally, CYP-SP concentration in the sample is calculated by substituting the value of ε and l constants in the equation, as well as the experimentally calculated value for total absorbance.

Determination of Kinetic Parameters for P22-CYP Pseudoviral Particles kCat and KM catalytic (apparent) constants were determined for the CYP encapsulated in P22 and the free CYP using as substrate both 2,6-DMP and H2O2. To calculate the kinetic parameters using 2,6-DMP as a substrate, two curves were constructed with two different concentrations of hydrogen peroxide, 5 mM and 60 mM. Reactions were carried out in 0.1 mL (50 mM Tris-HCl pH 8) with the following phenol concentrations: 10, 25, 50, 125, 250 and 500 µM. The reaction was started by adding 5 mM or 60 mM of $H_2O_2$. The amount of encapsulated enzyme used was 42.9 picomoles (assays with 5 mM $H_2O_2$) and 21.45 picomoles (assays with 60 mM $H_2O_2$); the amount of protein was determined by a concentration assay, specific for CYP450, for binding to CO. The catalytic activity was spectrophotometrically monitored at 468 nm ($\varepsilon_{468}$=14800 $M^{-1}$ $cm^{-1}$ using an Agilent 8453 UV-vis spectrophotometer. Catalytic constants were obtained through the GraphPad Prism 6 program.

For determination of kinetic parameters using free CYP, an amount of enzyme equal to 27.3 picomoles (assays with 5 mM $H_2O_2$) and 15 picomoles (assays with 60 mM $H_2O_2$) was used.

Regarding the determination of kinetic parameters using $H_2O_2$ as a substrate, a fixed concentration of 2,6-DMP equal to 500 µM was used for activity assays. Reactions were carried out in 0.1 mL (50 mM Tris-HCl pH 8) with the following peroxide concentrations: 1, 2, 5, 10, 20, 40 and 60 mM. The reaction was started by adding the corresponding amount of $H_2O_2$. The amount of encapsulated enzyme used was 42.9 and 21.45 picomoles; the amount of protein was determined by the concentration test, specific for CYP450, for binding to CO. Catalytic activity was spectrophotometrically monitored at 468 nm ($\varepsilon_{468}$=14800 $M^{-1}$ $cm^{-1}$) using an Agilent 8453 UV-vis spectrophotometer. Catalytic constants were obtained through the GraphPad Prism 6 program. For determination of kinetic parameters using free CYP, an amount of enzyme equal to 30 and 15 picomoles was used.

To determine the integrity of P22-CYP pseudo-viral particles in presence of 5 and 60 mM $H_2O_2$, 115 µg of dissolved particles were incubated in 100 µL (100 mM Tris-HCl pH 8) with the aforementioned hydrogen peroxide concentrations for 5 min. Subsequently, the capsid diameter was monitored by dynamic light scattering for 4 min.

Temperature Stability of P22-CYP Pseudo-Viral Particles

Stability of encapsulated CYP and the free enzyme was determined by measuring the percentage of activity retention at different times when the protein was incubated at 40 and 50° C. in a water bath. Incubation times for each of the temperatures were 0, 5, 10, 15 and 30 min. At the end of each time, an aliquot was removed from the sample, centrifuged for 1 min at 16,000×g and left to rest for 10 min to temper the sample before measuring activity. Catalytic activity was measured in a final volume of 0.1 mL in 100 mM Tris-HCl buffer pH 8 using 500 µM 2,6-DMP as substrate and initiating the reaction with 5 mM $H_2O_2$.

pH Activity Profile and Acid pH Stability of P22-CYP Pseudoviral Particles

To determine the activity profile at different pH values for the encapsulated and free enzyme, catalytic activity was measured at the following pHs: 5 (100 mM sodium acetate), 6 (100 mM potassium phosphate}, 7, 8 and 9 (100 mM Tris-HCl), 10 (100 mM borates). Catalytic activity was measured in a final volume of 0.1 mL using as substrate 500 µM 2,6-DMP and initiating the reaction with 5 mM $H_2O_2$.

The stability of encapsulated CYP and the free enzyme at acidic pH (pH 5 and 6) was determined by measuring the percentage of activity retention upon incubation of the protein at pH 5 and pH 6. The sample was incubated (at room temperature) for 1 and 16 h in 100 mM sodium acetate buffer for pH 5 and 100 mM potassium phosphate buffer for pH 6. At the end of each time, an aliquot was removed from the sample and centrifuged for 3 min at 16,000×g. Catalytic activity was measured in a final volume of 0.1 mL in 100 mM Tris-HCl buffer pH 8 using as substrate 500 µM 2,6-DMP and initiating the reaction with 5 mM $H_2O_2$.

Stability of P22-CYP Pseudoviral Particles to Protease Degradation

For proteolysis assays, the encapsulated and free enzyme was treated with 10 U of trypsin per mg protein, incubating for 1 and 20 h at room temperature. At the end of each time, an aliquot was taken out of the sample and the residual activity was measured in 100 mM Tris-HCl buffer pH 8 using 500 µM 2,6-DMP as substrate and initiating the reaction with 5 mM $H_2O_2$.

Determination of Iron Atoms in CYB-SP by ICP-MS

The amount of iron and sulfur in a sample of P22-CYP pseudo-viral particles is determined by mass spectrometry with inductively coupled plasma source (ICPMS), in order to calculate the number of CYPBM3 with heme incorporated in the structure. Sulfur is used as a reference to calculate the number of capsids per liter in the sample. The number of sulfur atoms per capsid is equal to 8401 (23 S for each CYP-SP and 14 S for each CP).

Taking into account that the limit of detection for Fe is 0.03 mg $L^{-1}$ and that of S is 0.1 mg $L^{-1}$, 21.6 mg of P22-CYP encapsulation were used to be above the detection limit for both atoms. The sample was incubated in concentrated nitric acid for 16 h at 70° C., once solubilized, the sample was taken to a final volume of 50 mL reaching a final concentration of 5% $HNO_3$ in mQ water. A sample with the same amount of buffer in which the protein was dissolved was also prepared as a control, brought to a final volume of 50 mL at a final concentration of 5% $HNO_3$ in mQ water.

Confinement Molarity and Capsid Occupation Percentage (CCMV and P22)

Enzyme concentration within the capsid, confinement molarity, was calculated by applying the following equation:

$$M_{conf} = \frac{(Enzymes_{per\ capsid})\left(\frac{1\ mol}{6.022 \times 10^{23}\ enzymes}\right)}{Internal\ volume_{capsid}}$$

Internal volume of P22 capsid is $5.8 \times 10^{-20}$ L (58000 $nm^3$) with an $r_{internal} = 24$ nm Percentage of capsid occupation by the enzyme was determined as follows:

$$\%\ Ocupación = \frac{(Enzymes_{per\ capsid})(Volume_{CYP})}{Internal\ volume_{capsid}} \times 100$$

CYPBM3 volume, 150.5 $nm^3$, was calculated by obtaining the average protein radius (3.3 nm) with support of the Maestro 9.6 software (Schrödinger, Inc.).

VLPs Analysis by Transmission Electron Microscope

6 µL of sample (about 100 µg $mL^{-1}$) were deposited on a copper grid covered with Formvar (Electron Microscopy Science). After 1 min, the remaining liquid was removed with a Whatman filter paper. 6 µL of 2% uranyl acetate was added to the grid, after 1 min the excess contrast agent was removed with filter paper. Samples were viewed with a JEOL JEM-2010 transmission electron microscope operated at 200 keV and equipped with a BioScan 600-W 1×1K digital camera mounted on the upper part.

In Vivo CYPBM3 Encapsulation Results in P22-CYP

In order to perform CYPBM3 encapsulation within the bacteriophage P22 capsid, the gene coding for the enzyme was fused with the nucleotide sequence of a truncated version of the scaffold protein (SP). This fragment comprising the C-terminal domain of the scaffold protein, and including amino acids 141 to 303, interacts with the coat proteins to catalyze, stabilize and direct the procapsid formation geometry. Specific oligonucleotides were designed to amplify 21B3 mutant CYPBM3 gene, adding NcoI and BamHI sites at the ends thereof, and then cloning it into the desired vector in phase with the la SP truncated gene.

Two different strategies were used for capsid production in vivo, CYP3M3-SP simultaneous expression and bacteriophage P22 coat protein (CP P22), and expression at different times of the two proteins. For the first strategy, the pETDuet plasmid was used in which both genes are under control of the same promoter. For the second strategy, genes were cloned in different vectors (pBAD-CYPBM3-SP and pRSF-CP P22) in order to induce genes differentially. For this case, the gene encoding the SP-enzyme was firstly expressed to subsequently carry out the induction of the coat protein gene.

The ease in the purification method involving only two steps (ultracentrifugation and gel filtration chromatography), results in high purity, which is an important advantage in VLPs production derived from P22 bacteriophage. For both protocols, differential coexpression and expression correctly assembled capsids were found with a gel filtration chromatography retention time, of around 65 min; however, proportion of correctly assembled capsids to aberrant species which elute from the column at 45 min, is different for each case (FIGS. 2A-2D).

These differences are due to differences in the different protocols implemented in expression, and therefore CYP-SP and CP P22 protein concentration as well as in the SP/CP P22 ratio, these two factors have an important influence on P22 capsid assembly.

Figure 3A:
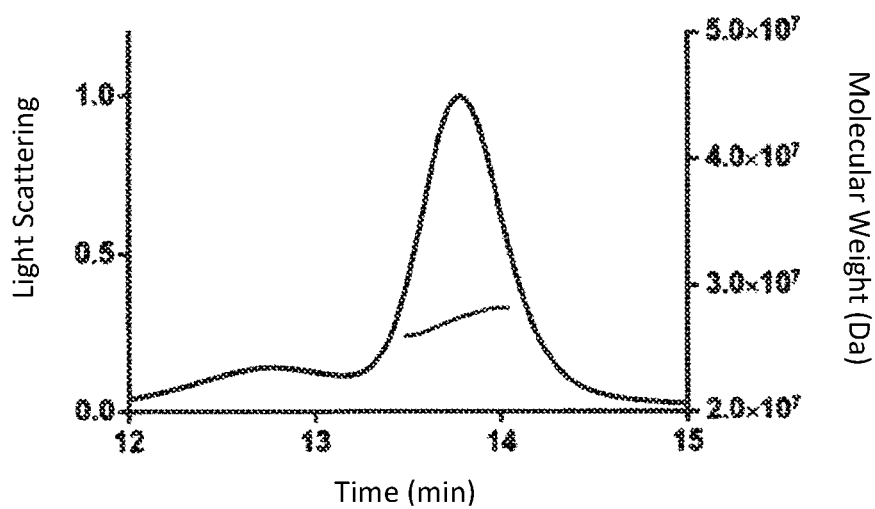
FIGS. 3A and 3B. Microphotography of P22 viral capsids where load or content of 90 to 150 molecules of cytochrome P450 per capsid is observed. Nanoparticle diameter is 53.6±2 nm. 3A) Analysis of molecular weight and P22-CYP encapsulation diameter by gel filtration chromatography (HPLC) coupled to MALS-QELS-RI detectors. 3B) P22-CYP particles seen at TEM. Negative staining FIG. 4. Catalytic activity of loaded nanoparticles with cytochrome P450 activity (CYP-P22 biocatalytic nanoparticle) compared to free-form enzyme: free CYP vs. CYP-P22 (5 mM $H_2O_2$).
Figure 3B:
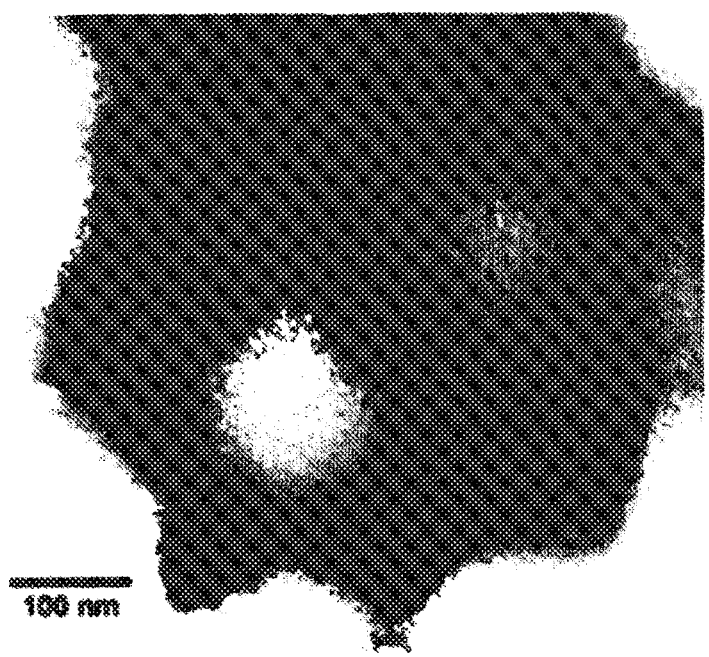

Obtained viral capsids (CYP-P22 nanoparticles) reached values of 120 mg/L of culture. The number of CYP molecules that can be loaded or contained in each capsid is from 90 to 150 molecules of CYP/capsid; more preferably 109.7±2.8 molecules of CYP/capsid, which results in a local enzyme concentration (confinement molarity=$M_{conf}$) of 3.14 mM. Obtained capsids are quasi-spherical and nanoparticle (CYP-P22) diameter was 53.6±2 determined by HPLC gel filtration chromatography coupled to multi-angle laser light scattering (MALS) detectors, quasi-elastic light scattering (QELS) and refractive index (RI). The presence of quasi-spherical capsids correctly assembled with CYP inside was verified by TEM (FIGS. 3A and 3B).

Example 3. Stability of P22-CYP Nanoparticles

Figure 15A:
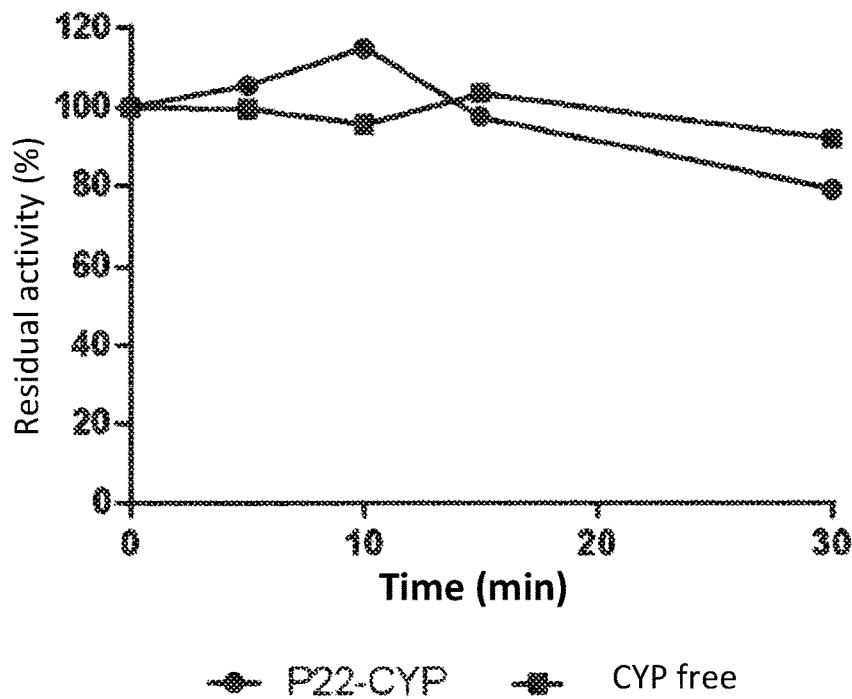
FIGS. 15A and 15B. Stability of free and encapsulated CYP in P22 at 40° C. (15A) and 50° C. (15B).
Figure 15:
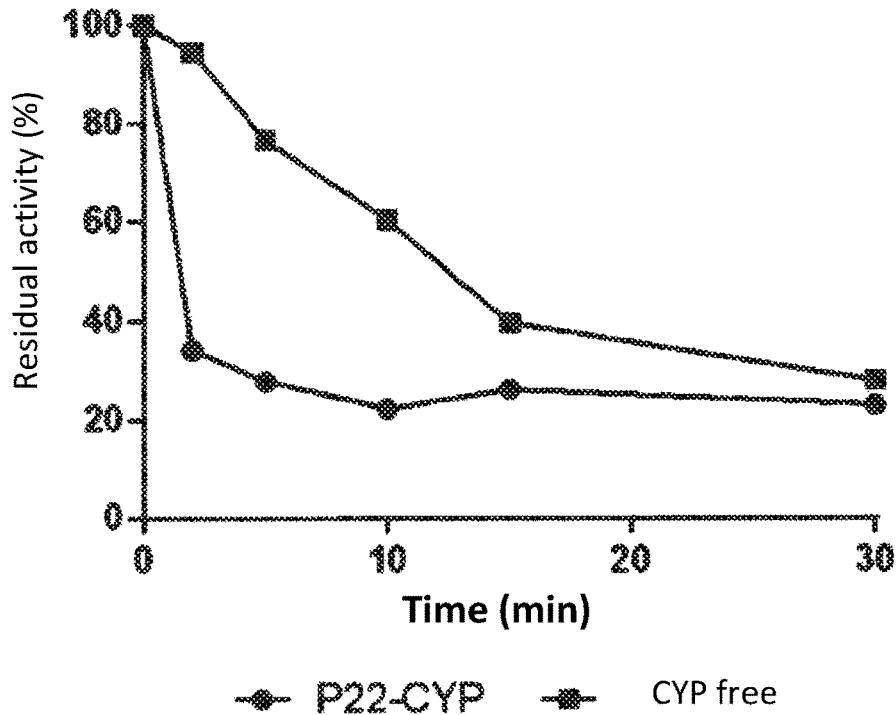

E) The stability of encapsulated CYP and the free enzyme was evaluated at two different temperatures: 40° C. and 50° C. The stability at 40° C. for the free and the encapsulated enzyme is practically the same, while at 50° C., the inactivation of the encapsulated enzyme was even faster than that found for free CYP (FIGS. 15A and 15B).

Figure 10:
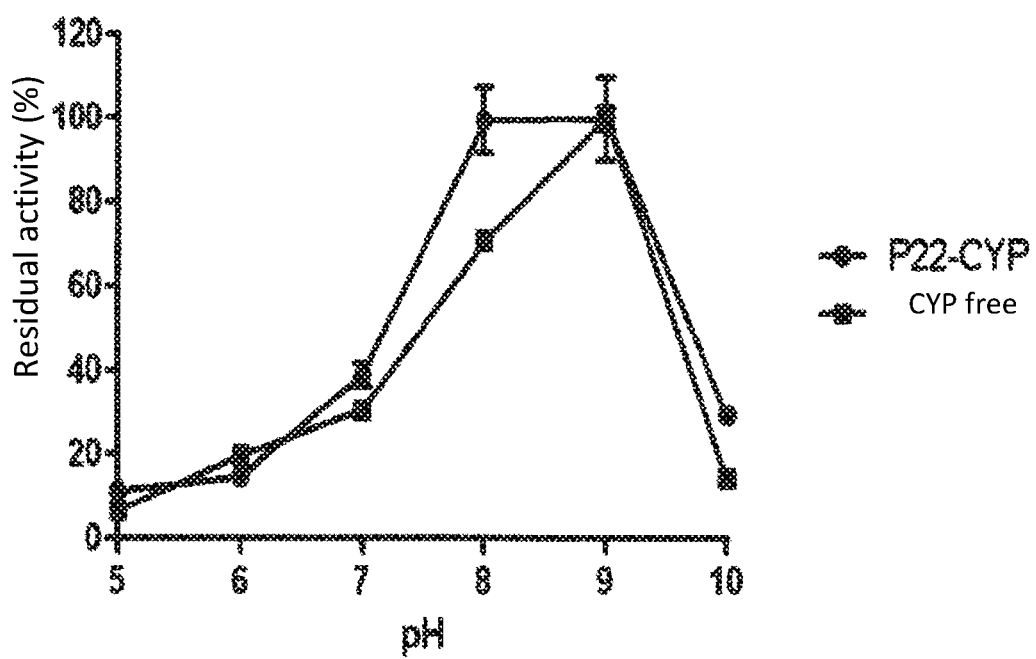
FIG. 10. Activity vs PH of CYP-P22 vs. free CYP
Figure 11:
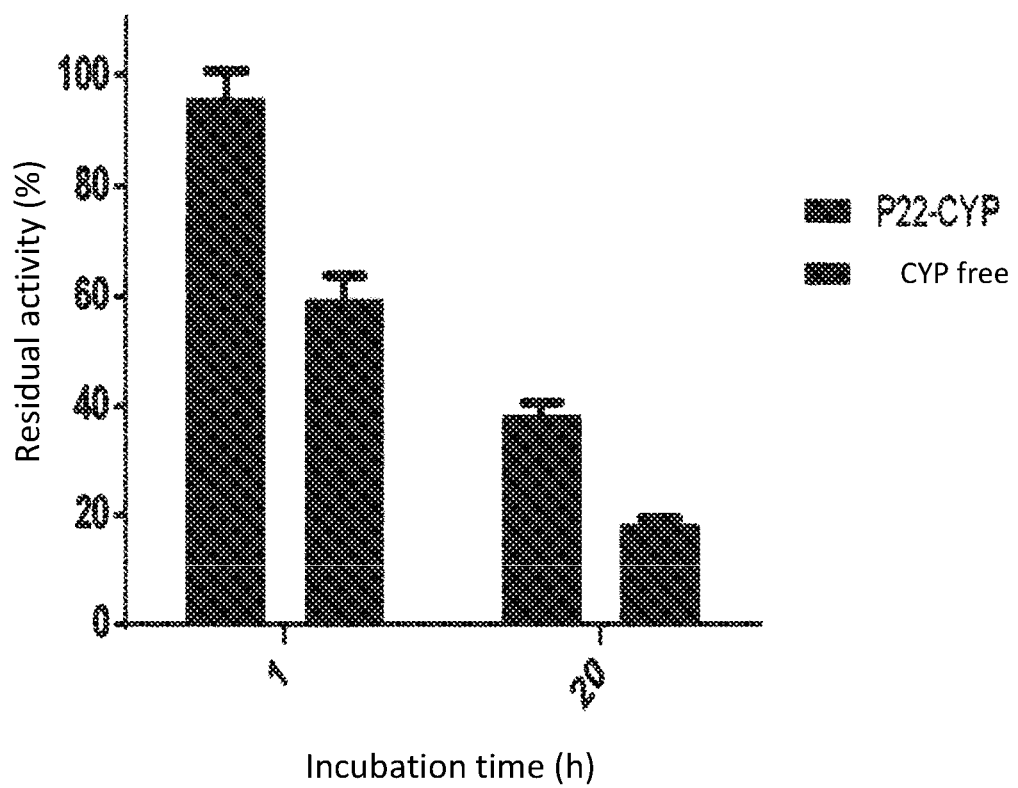
FIG. 11. Protease activity on CYP-P22 and free CYP

Activity profile was determined at different pH. As seen in the pH profile generated for the encapsulated and free enzyme, both graphs are very similar each other, with the exception of the optimum activity retention by one more pH unit (pH 8 and 9) for the P22-CYP case (FIG. 10). Due to virus intrinsic capacity to protect the material stored inside, stability of the encapsulated and free CYP in the presence of a protease was evaluated. After an hour of incubation with trypsin, the encapsulated enzyme retains practically all the activity (96%); while the free CYP loses 40%. After 20 hours of incubation the enzyme within the viral capsid retained 38% of the activity and the free CYP retained only 18% of its capacity to transform the substrate (FIG. 11).

Example 4. Immunogenicity of Biocatalytic Nanoparticles

F) Pegylation of the catalytic loaded nanoparticles is subsequently carried out. Modification with polyethylene glycol of the viral capsid surface is carried out with bifunctional polyethylene glycol. In this stage, nanoparticle safety was evaluated on the activation of different subpopulations of lymphoid cells. Likewise, the toxicity of the nanoparticles on these same lymphoid cells is measured.

Modification with polyethylene glycol of the viral capsid surface is carried out with maleimide polyethylene glycol ester of succinimide ester (Mal-PEG5000-NHS). The reaction is carried out at pH 8 with an excess of 5 on a molar basis to the capsid free amino acids.

Immunoassays are performed by ELISA technique, following the endpoint titration method. To this end, 96-well plates covered with nanoparticles suspended in cover buffer are used. After three successive washings using wash buffer (i.e., Concentrated Wash Buffer: sodium chloride 1.4 mol/l in buffer phosphates 100 mmol/l and nonionic surfactant 0.1 g/l), blocking buffer is applied into the wells (i.e., 3% Bovine Serum Albumin} for 1 h at 37° C. After three washes, 100 µL/rabbit serum well obtained at days 0, 10, 40, 70 is applied, as well as at the end of the immunization protocol (day 90), diluted serially with factor 2 from 1/1000 in the blocking buffer, and incubated for 1 h at 37° C. Plates are washed again and bound antibodies are detected using anti-rabbit IgG conjugated with alkaline phosphatase followed by the addition of the respective substrate (100 µL/well of p-nitrophenyl phosphate dissolved in Tris buffer). Serum titre is estimated as the inverse of the dilution thereof that produces 50% of the maximum absorbance recorded and data are compared with the titres obtained with CYP without modification.

Safety of CYP-P22 (nanoparticles loaded with cytochrome P450 activity) on activation of different lymphoid cell subpopulations is evaluated. For such end, peripheral blood mononuclear cells isolated from healthy blood bank donors are incubated in the presence of different amounts of nanoparticles for 24 or 48 hours and cytosine or chemokine secretion is quantified from culture supernatant by a multiplex assay with beads coupled to a panel of specific antibodies against these analytes.

Example 5. Targeting of Biocatalytic CYP-P22 (Nanoparticles Loaded with Cytochrome P450 Activity)

G) Loaded nanoparticles are functionalized for targeting breast tumor cells, tumor tissues or other tissue of interest with a cyclic peptide or another ligand.

To synthesize CYP-P22 (loaded nanoparticles) functionalized with Arg-Ala-Asp-D-Phe-Cys cyclic peptide (SEQ ID NO: 5) to be recognized by the integrin αvβ3/5 of the breast tumor cells. Two peptide equivalents are added to the reaction mixture under gentle stirring for 12 h. The reaction product is expressed against a phosphate buffer.

Example 6. Catalytic Activity

Figure 4:
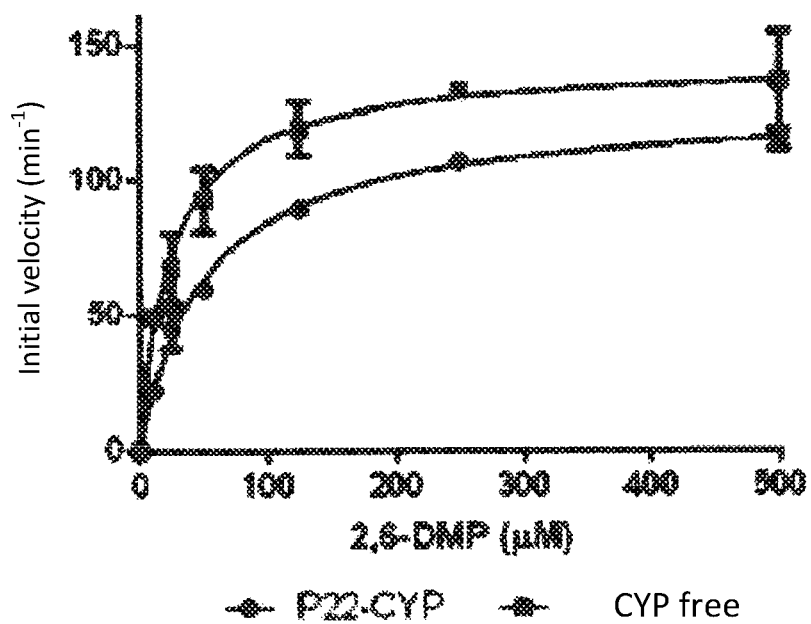

H) Catalytic capacity of P22 capsids with CYP inside is evaluated. Reactions were carried out in 0.1 mL (50 mM Tris-HCl pH 8) with the following phenol concentrations: 10, 25, 50, 125, 250 and 500 µM. The reaction was started by adding 5 mM or 60 mM of $H_2O_2$. The amount of encapsulated enzyme used was 42.9 picomoles, the amount of protein was determined by a CO binding assay specific for CYP450. Catalytic activity was spectrophotometrically monitored at 468 nm ($\varepsilon468$=14800 $M^{-1}$ $cm^{-1}$). The enzyme encapsulated in this VLP is catalytically active using 2,6-DMP and $H_2O_2$ as substrates (FIG. 4). For calculations, the CYP concentration determined by the CO (catalytically active protein) assay is taken into account. The encapsulated enzyme follows a Michaelis-Menten kinetics as does free CYP. The CYP 450 loaded nanoparticle-bacteriophage P22 nanocapsid has the following constants with respect to free CYP.

TABLE 3

CYP-P22 and free CYP Kinetics.

| | 2,6-DMP (5 mM $H_2O_2$) | | |
|---|---|---|---|
| | $k_{cat\ app}$ ($min^{-1}$) | $K_{M\ app}$ (mM) | $k_{cat}/K_M$ ($min^{-1}$ $\mu M^{-1}$) |
| CYP-P22 | 127.2 (±2.3) | 51.1 (±3.2) | 2.5 |
| CYP free | 143.6 (±4.6) | 24.9 (±3.3) | 5.8 |

Example 7. Transformation of Prodrugs with CYP

Figure 5:
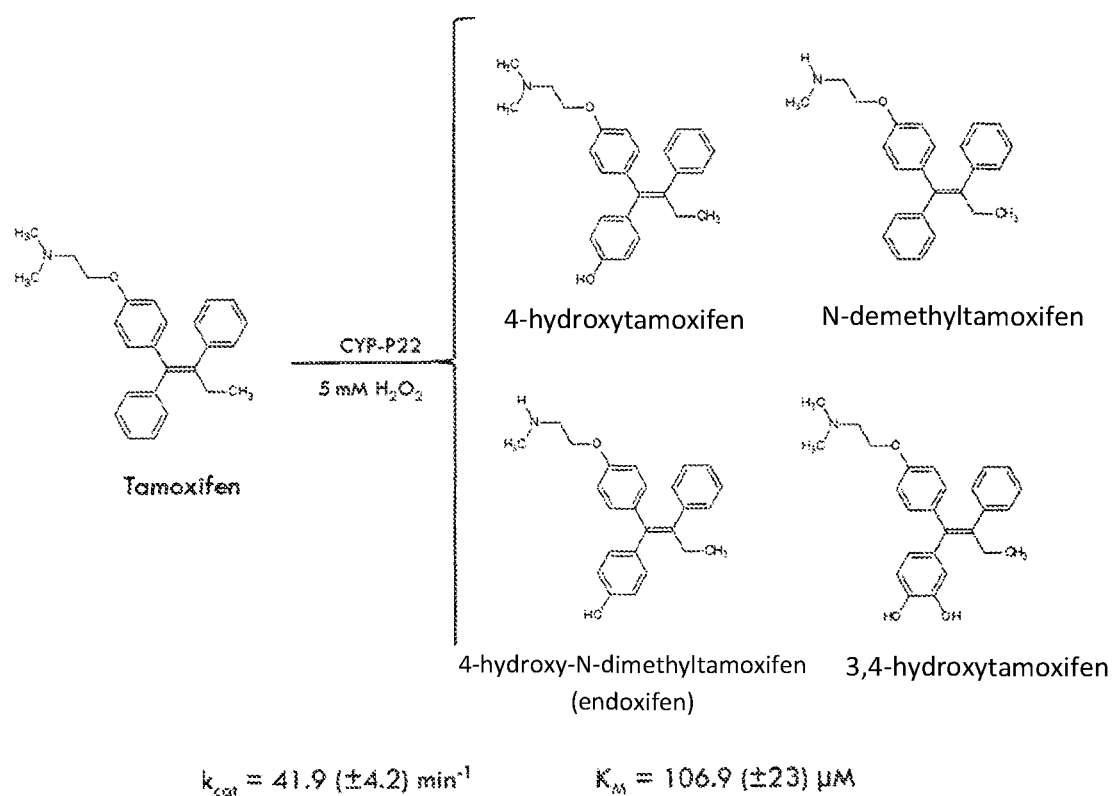
FIG. 5. Tamoxifen transformation products catalyzed by P22 nanoparticles containing cytochrome P450 (CYP-P22 biocatalytic nanoparticle). Transformation products are: 4-hydroxy tamoxifen; N-demethyltamoxifen; 4-hydroxy-N-dimethyltamoxifen (endoxifen); 3,4-hydroxytamoxifen.
Figure 6:
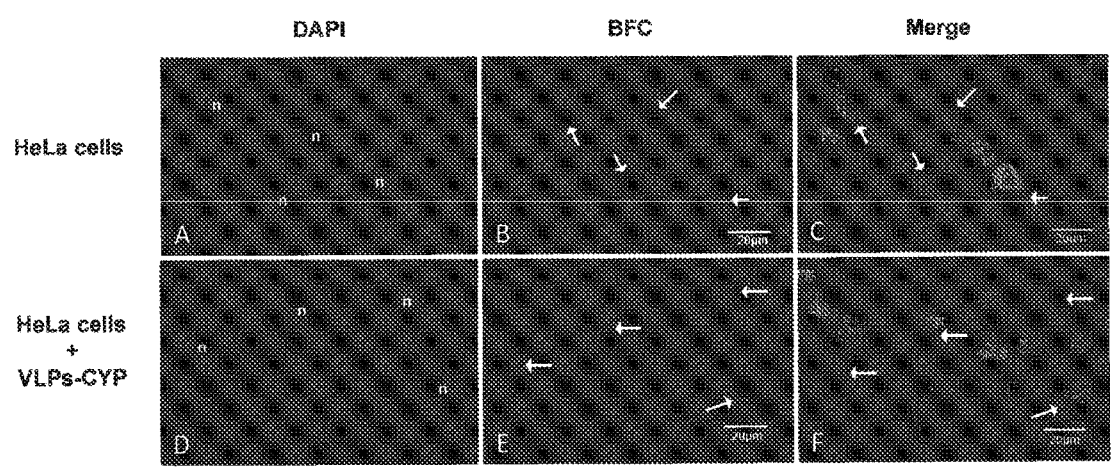
FIGS. 6A-6F. Cytochrome P450 activity in human cervical carcinoma cells treated with VLPs-CYP. Staining with DAPI shows cell nuclei marked with "n", panels 6A and 6D. Endogenous CYP activity on BFC reagent in untreated cells, panel 6B. Increase in CYP activity in cells treated with VLPs-CYP, panel 6E. BFC reagent is transformed into a fluorescent product {HFC) and is located in cell cytoplasm (white arrows). Overlapping of images stained with DAPI and with BFC, panels 6C and 6F. Cells were observed with a 63× objective (DIC), 1.4 NA of planar-apochromatic oil immersion.
Figure 7:
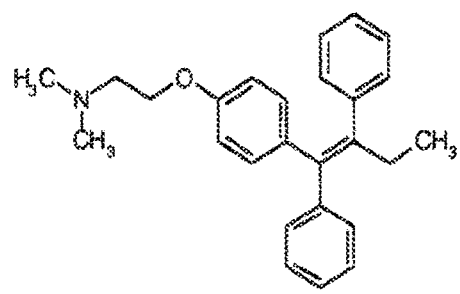
FIG. 7. Tamoxifen transformation (a prodrug used for treatment of breast cancer) by CYP-P22 (biocatalytic nanoparticles) containing cytochrome P450.
Figure 7:
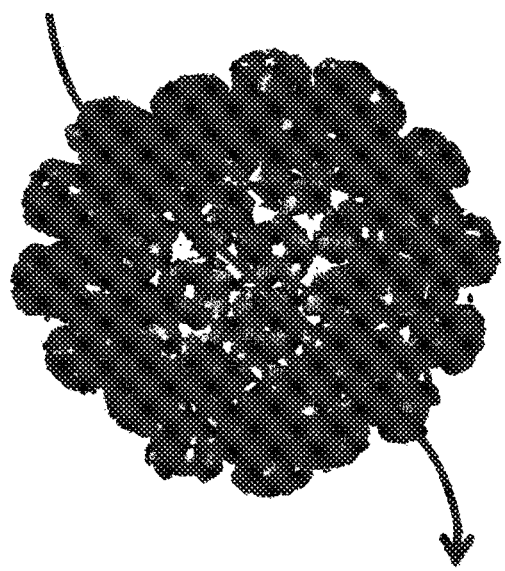

A determination of expressed and purified CYP enzymatic activity, for example by means of tamoxifen transformation, is shown in FIG. 5. Reactions will be initiated by adding 5 mM of $H_2O_2$ or glucose oxidase+glucose and reaction progress is monitored by HPLC equipped with a C18 reverse phase column. The reactions are carried out in a final volume of 0.5 mL (100 mM potassium phosphate buffer pH 7.4, 2 mM ascorbic acid) with the following substrate concentrations: 20, 40, 80, 140 and 200 µM. Methanol concentration in the reaction (the solvent in which tamoxifen is dissolved) was always the same (1%). The enzyme amount to be used per test was between 90 and 225 picomoles. Reactions are initiated by adding 5 mM $H_2O_2$, or glucose oxidase, and carried out at 25° C. for 5 min. Reactions are terminated by adding 50 uL of acetic acid to be subsequently centrifuged (3 min at 13,000 rpm) and analyzed by HPLC following the elution gradient below: 0 to 10 min solvent B 40%, 10 to 20 min solvent B up to 65% with a flow of 0.75 mL min-1. Mobile phase A consists of a 10 mM ammonium acetate buffer (pH 3) and mobile phase B, 100% acetonitrile. Decrease in tamoxifen peak is monitored at 280 nm.

Bacterial CYP is capable of transforming the drug into four products (FIG. 5), which are detected by liquid nanochromatography coupled to tandem mass spectrometry (nanoLC/MSMS). Identified compounds correspond to 4-hydroxytamoxifen, 4-hydroxy-N-demethyltamoxifen (endoxifen), Ndemethyltamoxyphen and dihydroxy tamoxifen. It is important to mention that control of tamoxifen with hydrogen peroxide (without enzyme) does not generate any product profile.

Example 8. Affinity and Efficiency of CYP-P22 Biocatalytic Nanoparticles

J) Affinity evaluation of functionalized loaded nanoparticles in tumor cells in vitro is carried out in human MCF7 breast cancer cells that are maintained in DMEM medium (Dulbecco's Modified Eagle's Medium) supplemented with 10% fetal bovine serum. Cells are cultured at 37° C. in 5% $CO_2$ and before treatment with nanoparticles (CYP-P22), cells are washed twice with serum-free medium and then 1 mL of serum-free medium will be added. Subsequently, functionalized nanoparticles are added to each well and incubated by 4 hours. After incubation, supernatant is removed and 1 mL of fresh medium containing 10% fetal bovine serum is incubated for further 48 hours. The presence of biocatalytic nanoparticles (CYP-P22) with CYP activity is evaluated in the transformation of 7-benzyloxy-4-trifluoromethyl-coumarin (BFC) monitored by fluorescence according to the method of Donato et al. [58]. Fluorescence assay for determining CYP activity is performed with direct incubation of cultured tumor cells in a 12-well plate in the presence of 100 µM of BFC (FIG. 6A-6F). BFC is added dissolved in acetonitrile, ensuring that final acetonitrile concentration in the wells does not exceed 0.5% (v/v). After 60 min of incubation at 37° C. the incubation medium is removed and conjugated products of CYP transformation will be hydrolyzed with a mixture of 3-glucuronidase/arylsulfatase for 2 hours at 37° C. Finally, samples are diluted with the corresponding solution and product (7-hydroxy-4-trifluoromethylcoumarin, HFC) fluorescence is quantified in a spectrofluorimeter with 410 nm excitation and 510 nm emission. DAPI staining shows "n"-labeled cell nuclei, panels 6A and 6D. Endogenous CYP activity on BFC reagent in untreated cells, panel 6B. Increased CYP activity in cells treated with CYP-P22, panel 6E. BFC reagent is transformed into a fluorescent product (HFC) and is located in cell cytoplasm (white arrows). Overlapping of DAPI and BFC stained images, panels 6C and 6F. Cells were observed with a 63X objective (DIC), 1.4 NA of plan-apochromatic oil immersion.

Images clearly show that cytochrome P450 activity in tumor cells treated with biocatalytic nanoparticles (CYP-P22) is much greater than that found endogenously in untreated cells.

Nanoparticle efficiency in prodrug activation is carried out by determining the viability of previously treated tumor cells with nanoparticles in the presence of the prodrug or in combination with a prodrug selected from: tamoxifen, resveratrol, tegafur, ifosfamide, clopidogrel, nabumetone, pafuramidine, loratadine.

INDUSTRIAL APPLICABILITY

The present invention relates to a therapeutic strategy based on nanotechnology that incorporates or loads the cytochrome P450 in a nanoparticle or nanocapsid, which in turn carries this cytochrome P450 enzymatic activity to a tissue of interest; for example, in tumor cells, tumor tissues or others allowing a greater efficiency in the prodrug activation through CYP. The matter above, contributes in the treatment of cancer, provides greater efficiency of cancer treatment with chemotherapy or in other treatments where the prodrug is activated by cytochrome P450, a decrease in the medication doses required and a decrease in side effects. With this, increase the local concentration of active drug in the vicinity of tumor cells or tissues of interest, increasing the concentration of active drug and therefore the drug efficiency in tumor or target tissue and reducing the toxicity produced by the drug in the rest of the body cells.

REFERENCES

1. Wild C. P. (2012) The role of cancer research in noncommunicable disease control JNCI *J. Natl. Cancer Inst.* 104:1051-1058.
2. McWhirter D., Kitteringham, N., Jones, R. P., Malik, H. Park, K., Palmer, D, (2013) Chemotherapy induced hepatotoxicity in metastatic colorectal cancer: A review of mechanisms and outcomes. *Crit. Rev, Oncol. Hematol.* [Epub ahead of print].
3. McFadyen M, Melvin W, Murray G I. (2004). Cytochrome P450 enzymes: Novel options for cancer therapeutics. *Mol. Cancer Therap.* 3:363-371.
4. Huttunen K, Mähönen N, Raunio H, Rautio J. (2008), Cytochrome P450-Activated Prodrugs: Targeted Drug Delivery. *Cur. Med. Chem.* 15:2346-2365.
5. Choudhary, D., I. Jansson, et al. (2003). Comparative expression profiling of 40 mouse cytochrome P450 genes in embryonic and adult tissues. *Arch. Biochem. Biophys.* 414:91-100.
6. Zhao, Y. N., Zhang, W., Chen, Y-C, Fang, X-Q. and Hide, L (2012). Relative imbalances in the expression of catechol-O-methyltransferase and cytochrome P450 in breast cancer tissue and their association with breast carcinoma. *Maturitas.* 72:139-145
7. (a) Huttunen, K. M., N. Mahonen, et al. (2008). Cytochrome P450-activated prodrugs: targeted drug delivery. *Curr. Med. Chem.* 15:2346-2365. (b) Ravichandran K G, Boddupalli S S, Hasermann C A, Peterson J A, Deisenhofer J. (1993), Crystal structure of hemoprotein domain of P450BM-3, a prototype for Microsomal P450's, Science 261: 731-736, (c) Anzenbacherová E, Bec N, Anzenbacher P, Hudecek J, Soucek P, Jung C, Munro A, Lange R. {2000}. Flexibility and stability of the structure of cytochromes P450 3A4 and BM3. European Journal of Biochemistry 267: 2916-2920. (D) Whitehouse C, Bell S G, Tufton H G, Kenny R J, Ogilvie L C, Wong L L. (2008). Evolved CYP102A1 (P450BM3) variants oxidize a range of non-natural substrates and offer new selectivity options, Chemical Communications 8: 966-968. (e) Di Nardo G, Fantuzzi A, Sideri A, Panicco P, Sassone C, Giunta C, Gilardi G. (2007). Wild-type CYP102A1 as a biocatalyst: turnover of drugs usually metabolized by human liver enzymes. Journal of Biological Inorganic Chemistry 12: 313-323, 8. Al-Lazikani B, Banerji U, Workman P. (2012). Combinatorial drug therapy for cancer in the post-genomic era. *Nature Biotechnol.* 30:679-692.
9. Hetch J, Waxman D. (2000). Selection of Cytochrome P450 Genes for Use in Prodrug Activation-Based Cancer Gene Therapy. *Meth. Mol. Med.* 35:77-83.
10. Xu G, McLeod H. (2001). Strategies for Enzyme/Prodrug Cancer Therapy. *Clin. Cancer Res.* 7:3314-3324.
11. Niculescu-Duvaz I, Springer C J. (1997). Antibody-directed enzyme prodrug therapy (ADEPT): a review. *Adv. Drug Delivery Rev.* 26:151-172.
12. Francis R J, Sharma S K, Springer C, Green A J, Hope-Stone L D, Sena L, Martin J, Adamson K L, Robbins A, Gumbrell L, O'Malley D, Tsiompanou E, Shahbakhti H, Webley S, Hochhauser D, Hilson A J, Blakey D, Begent R H. (2002). A phase I trial of antibody directed enzyme prodrug therapy (ADEPT) in patients with advanced colorectal carcinoma or other CEA producing tumours. *Brit. J. Cancer* 87: 600-607.
13. Dachs G U, Tupper J, Tozer G M. (2005). From bench to bedside for gene-directed enzyme prodrug therapy of cancer. Anticancer Drugs 16: 349-359.
14. Girino P, Arnold F. (2003). A Self-Sufficient Peroxide-Driven Hydroxylation Biocatalyst. *Angew. Chem, Int. Ed.* 42: 3299-3301.
15. Sánchez-Sánchez L., Cadena R. D., Palomares L. A., Ruiz-Garcia J., Koay M. S. T., Cornelissen J. J. M. T. and Vazquez-Duhalt R. (2014) Chemotherapy pro-drug activation by biocatalytic virus-like nanoparticles containing cytochrome P450. *Enzyme Microb. Technol.* 60:24-31.
16. Vidal-Limón, A., Águila, S., Ayala, M., Batista, C. V., Vazquez-Duhalt, R. (2013). Peroxidase activity stabilization of cytochrome P450BM3 by rational analysis of intramolecular electron transfer. *J. Inorg. Biochem.* 122: 18-26.
17. Lee A, Z Niu, Wang Q. (2009), Viruses and Virus-Like Protein Assemblies-Chemically Programmable Nanoscale Building Blocks. *Nano Res,* 2: 349-364.
18. Strable E, Finn M G. (2009). Chemical Modification of Viruses and Virus-Like Particles. *Curr. Topics Microbiol. Immunol.* 327:1-18.
19. Bamford D H, Grimes J M, Stuar D I, (2005). What does structure tell us about virus evolution? *Curr. Op Struct. Biol.* 15:655-663.
20. Douglas T, Young M. (2006). Viruses: Making friends with old foes. *Science* 312: 873-875.
21. Hooker J, Datta A, Botta M, Raymond K N, Francis M B. (2007). Magnetic Resonance Contrast Agents from Viral Capsid Shells: A Comparison of Exterior and Interior Cargo Strategies. *Nano Lett.* 7:2207-2210.
22. Ren Y, Wong S, Lim L. (2007). Folic Acid-Conjugated Protein Cages of a Plant Virus: A Novel Delivery Platform for Doxorubicin. *Bioconjugate Chem.* 18:836-843.
23. Verma I, Weitzma M. (2005). Gene therapy: Twenty-first century medicine. *Ann. Rev. Biochem.* 74: 711-738.
24. Lipin D I, Chuan Y P, Lua L H, Middelberg A P. (2008). Encapsulation of DNA and non-viral protein changes in the structure of murine polyomavirus virus-like particles, *Arch. Virol.* 153:2027-39.
25. Günther C, Schmidt U, Rudolph R, Böhm G. (2001). Protein and peptide delivery via engineered polyomavirus-like particles, *FASEB J,* 15: 1646-1648
26. Abbing A, Blaschke U, Grein S, Kretschmar M, Stark C M B, Thies M J W, Walter J, Weigand M, Woith D C, Hess J, Reiser C O A. (2004). Efficient intracellular delivery of a protein and a low molecular weight substance via recombinant polyomavirus-like particles, *J. Biol. Chem.* 279:27410-27421.
27. Minten I J, Nolte R J, Cornelissen J J. (2010), Complex assembly behavior during the encapsulation of green fluorescent protein analogs in virus derived protein capsules. *Macromol. Biosci.* 10: 539-545.
28. O'Neil A, Prevelige P E, Basu G, Douglas T. (2012). Coconfinement of fluorescent proteins: spatially enforced communication of GFP and mCherry encapsulated within the P22 capsid. *Biomacromolecules* 13: 3902-3907.
29. Iyer A K, Khaled G, Fang J, Maeda H. (2006). Exploiting the enhanced permeability and retention effect for tumor targeting, *Drug Discovery Today* 11: 812-818,
30. Torchilin V. (2011). Tumor delivery of macromolecular drugs based on the EPR effect. *Adv. Drug Delivery Rev.* 63:131-135.
31. Teschke C, Parent K. (2010). 'Let the phage do the work': Using the phage P22 coat protein structures as a framework to understand its folding and assembly mutants. *Virology* 401: 119-130.
32. Thuman-Commike P A, Greene B, Jakana J, Prasad B V, King J, Prevelige P E Jr, Chiu W. (1996). Three-dimensional structure of scaffolding-containing phage p22 procapsids by electron cryo-microscopy. *J. Mol. Biol.* 260: 85-98.
33. Chen D H, Baker M L, Hryc C F, DiMaio F, Jakana J, Wu W, Dougherty M, Haase-Pettingell C, Schmid M F, Jiang W, Baker D, King J A, Chiu W. (2011). Structural basis for scaffolding—mediated assembly and maturation of dsDNA virus. *Proc. Nat. Acad. Sci. USA* 108: 1355-1360.
34. Parent K N, Khayat R, Tu L H, Suhanovsky M M, Cortines J R, Teschke C M, Johnson J E, Baker T S. (2010). P22 coat protein structures reveal a novel mechanism for capsid maturation: stability without auxiliary proteins or chemical crosslinks. *Structure* 18: 390-401.
35. Fiedler J, Brown S, Brown S D, Lau J L, Finn M G. (2010). RNA-directed packaging of enzymes within virus-like particles. *Angew. Chem. Int. Ed.* 49: 9648-9651.
36. O'Neil A, Prevelige P E, Douglas T. (2013). Stabilizing viral nano-reactors for nerve-agent degradation. *Biomaterials Sci.* 1:881-386.
37. Inoue T, Kawano M A, Takahashi R U, Tsukamoto H, Enomoto T, Imai T, Kataoka K, Handa H. (2008), Engineering of SV40-based nano-capsules for delivery of heterologous proteins as fusions with the minor capsid proteins VP2/3. *J. Biotechnol.* 134:181-192.
38. Rodríguez P L, Harada T, Christian D A, Pantano D A, Tsai R K, Discher D E. (2013). Minimal self peptides that inhibit phagocytic clearance and enhance delivery of nanoparticles. *Science* 339: 971-975.
39. Kreppel F, Kochanek S. (2008). Modification of adenovirus gene transfer vectors with synthetic polymers: a scientific review and technical guide. *Mol. Ther.* 16:16-29.

40. Comellas-Aragonés M, Engelkamp H, Claessen V I, Sommerdijk N A, Rowan A E, Christianen P C, Maan J C, Verduin B J, Cornelissen J J, Nolte R J. (2007). A virus-based single-enzyme nanoreactor. *Nature Nanotechnol.* 2:635-639.
41. Minten I J, Claessen V, Blank, Rowan A E, Nolte R J, Cornelissen J J. (2011). Catalytic capsids: the art of confinement. *Chem. Sci.* 2:358-362.
42. Patterson D, Prevelige P, Douglas T. (2012). Nanoreactors by programmed enzyme encapsulation inside the capsid of the bacteriophage P22. *ACS Nano* 6: 5000-5009.
43. Patterson D, Shwarz B, El-Boubbou K, Oost J, Prevelige P, Douglas T. (2012), Virus-like particle nanoreactors: programmed encapsulation of the thermostable CelB glycosidase inside the P22 capsid. *Soft Matter* 8: 10158-10166.
44. Patterson D P, Schwarz B, Waters R S, Gedeon T, Douglas T. (2014). Encapsulation of an Enzyme Cascade within the Bacteriophage P22 Virus-Like Particle. *ACS Chem. Biol.* 9:359-365.
45. Glasgow J, Caperhart S, Francis M B, Tullman-Ercek D. Osmolyte-mediated encapsulation of proteins inside MS2 viral capsids. *ACS Nano* 2012; 6: 8658-67.
46. Kreppel, F., Kochanek, S. (2008). Modification of Adenovirus Gene Transfer Vectors With Synthetic Polymers: A Scientific Review and Technical Guide. *Mol. Therapy* 16: 16-19.
47. An, Q., Lei, Y., Jia, N., Zhang, X., Bai, Y., Yi, J., Chen, R., Xia, A., Yang, J., Wei, S., Cheng, X., Fan, A., Mu, S., Xu, Z. (2007). Effect of site-directed PEGylation of trichosanthin on its biological activity, immunogenicity, and pharmacokinetics. *Biomol. Eng.* 24:643-649.
48. Akhtar, J., Mallaredy, V., Dandapat, J., Maiti, P., Sahoo, S., Singh, S. (2012). PEGylation of an osteoclast inhibitory peptide: Suitable candidate for the treatment of osteoporosis. *Int. J. Pharm.* 15:429-436.
49. da Silva Freitas, D., Mero, A., Pasut, G. (2013). Chemical and Enzymatic Site Specific PEGylation of hGH. *Bioconjug. Chem.* 24:456-463.
50. Cai, W., Shin, D. W., Chen, K., Gheysens, O., Cao, Q. Wang, S. X., Gambhir, S. S., Chen, X. (2006). Peptide-labeled near-infrared quantum dots for imaging tumor vasculature in living subjects. *Nano Lett.* 6:669-676.
51. Huang, R., Ke, W., Han, L., Li, J., Liu, S., Jiang, C. (2011). Targeted delivery of chlorotoxin-modified DNA-loaded nanoparticles to glioma via intravenous administration. *Biomaterials* 32: 2399-23406.
52. Hoskins J M, Carey L A, McLeod H L. (2009). CYP2D6 and tamoxifen: DNA matters in breast cancer. Nature Reviews Cancer 9: 576-586.
53. Osborne C K. (1998). Tamoxifen in the treatment of breast cancer. New England Journal of Medicine 339: 1609-1618.
54. Rochat B. (2005). Role of cytochrome P450 activity in the fate of anticancer agents and in drug resistance: focus on tamoxifen, paclitaxel and imatinib metabolism. Clinical Pharmacokinetics 44: 349-366.
55. Brauch H, Mürdter T, Eichelbaum M, Schwab M. (2009). Pharmacogenomics of Tamoxifen Therapy. Clinical Chemistry 55: 1770-1782.
56. Pirola L, Fröjdö S. (2008). Resveratrol: one molecule, many targets. International Union of Biochemistry and Molecular Biology Life 60: 323-332.
57. Lin L L, Lien C Y, Cheng Y C, Ku K L. (2007). An effective sample preparation approach for screening the anticancer compound piceatannol using HPLC coupled with UV and fluorescence detection. Journal of Chromatography B 853: 175-182.
58. Donato, M. T., Jiménez, N. Castell, J. V. and Gómez-Lechón M. J. (2004) Fluorescence-based assay for screening nine cytochrome P450 activities in intact cells expressing individual human P450 enzymes. *Drug Metab. Disp.* 32:600-670.

---

The invention claimed is:

1. An immunologically inert and functionalized CYP-P22 biocatalytic nanoparticle that activates prodrugs in a target cell, comprising
   a) a polypeptide sequence of SEQ ID NO:4 which is a fusion of a scaffold protein SP and a CYPBM3 protein,
   b) a fragment of a P22 scaffold protein,
   c) a coat protein of P22 bacteriophage,
   d) a bifunctional dendritic polyethylene glycol, and
   e) a cyclic polypeptide of SEQ ID NO: 5.

2. The CYP-P22 biocatalytic nanoparticle according to claim 1, wherein the CYP-P22 biocatalytic nanoparticle measures 53.6±2 nm in diameter.

3. The CYP-P22 biocatalytic nanoparticle according to claim 1, wherein the CYP-P22 biocatalytic nanoparticle comprises from 90 to 150 molecules of CYP/capsid.

4. The CYP-P22 biocatalytic nanoparticle according to claim 1, wherein the prodrug is selected from: tamoxifen, resveratrol, tegafur, ifosfamide, clopidogrel, nabumetone, pafuramidine, and loratadine.

5. The CYP-P22 biocatalytic nanoparticle according to claim 1, wherein the target cell comprises mammalian or human patient tissues.

6. The CYP-P22 biocatalytic nanoparticle according to claim 5, wherein the tissue presents a tumor mass.

7. The CYP-P22 biocatalytic nanoparticle according to claim 6, wherein the tumor mass is a cancer selected from: breast cancer, and colon cancer.

8. An immunologically inert and functionalized CYP-P22 biocatalytic nanoparticle that activates prodrugs in a target cell, for the manufacture of a medicine useful for contributing in the treatment of cancer of a mammalian or human patient, comprising:
   a) a polypeptide sequence of SEQ ID NO:4 which is a fusion of a scaffold protein SP and a CYPBM3 protein,
   b) a fragment of a P22 scaffold protein,
   c) a coat protein of P22 bacteriophage,
   d) a bifunctional dendritic polyethylene glycol, and
   e) a cyclic polypeptide of SEQ ID NO: 5.

9. The CYP-P22 biocatalytic nanoparticle according to claim 8, wherein the CYP-P22 biocatalytic nanoparticle is 53.6±2 nm in diameter.

10. The CYP-P22 biocatalytic nanoparticle according to claim 8, wherein the CYP-P22 biocatalytic nanoparticle comprises from 90 to 150 molecules of CYP/capsid.

11. The CYP-P22 biocatalytic nanoparticle according to claim 8, wherein the prodrug is selected from: tamoxifen, resveratrol, tegafur, ifosfamide, clopidogrel, nabumetone, pafuramidine, and loratadine.

12. The CYP-P22 biocatalytic nanoparticle according to claim 8, wherein the target cell comprises tissues from a mammalian or human patient.

13. The CYP-P22 biocatalytic nanoparticle according to claim 12, wherein the tissue presents a tumor mass.

14. The CYP-P22 biocatalytic nanoparticle according to claim 13, wherein the tumor mass is a cancer selected from: breast cancer, and colon cancer.

15. The CYP-P22 biocatalytic nanoparticle according to claim 1, wherein the CYP-P22 is in combination with a prodrug.

16. The CYP-P22 biocatalytic nanoparticle according to claim 15, wherein the prodrug is selected from: tamoxifen, resveratrol, tegafur, ifosfamide, clopidogrel, nabumetone, pafuramidine, and loratadine.

17. The CYP-P22 biocatalytic nanoparticle according to claim 1, wherein the prodrug is selected from: tamoxifen, resveratrol, tegafur, isosfamide, clopidogrel, nabumetone, pafuramidine, and loratadine.

* * * * *

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: Inhibitor Peptide

<400> SEQUENCE: 1

Asp Arg Gln Ile Lys Ile Trp Phe Gln Asn Arg Arg Met Lys Trp Lys
1               5                   10                  15

<210> SEQ ID NO 2
<211> LENGTH: 33
<212> TYPE: DNA
<213> ORGANISM: Artificial Sequence
<220> FEATURE:
<223> OTHER INFORMATION: Forward primer

<400> SEQUENCE: 2
aaaaatcatg ccatggcaat taaagaaatg cct                                  33

<210> SEQ ID NO 3
<211> LENGTH: 32
<212> TYPE: DNA
<213> ORGANISM: Artificial Sequence
```

<220> FEATURE:
<223> OTHER INFORMATION: Reverse primer

<400> SEQUENCE: 3
aaaaaagcgg gatccagtgc taggtgaagg aa                                32

<210> SEQ ID NO 4
<211> LENGTH: 634
<212> TYPE: PRT
<213> ORGANISM: Artificial Sequence
<220> FEATURE:
<223> OTHER INFORMATION: Fusion Protein

<400> SEQUENCE: 4

```
Met Ala Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Val Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala Arg Asn Ile Leu Leu Pro Ser Leu Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ser Asp Glu Lys Ile Glu Val Pro Glu
    130                 135                 140

Asp Val Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asp Leu Val Asp Lys Ile Ile Ala Asp Arg Lys
    210                 215                 220

Ala Ser Gly Glu Gln Ser Asp Asp Leu Leu Thr His Met Leu His Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Thr Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335
```

```
Glu Asp Thr Val Leu Gly Gly Glu Tyr Pro Leu Lys Gly Asp Glu
                340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Glu Glu Thr Leu Thr Leu Lys Pro Glu Gly Phe Val Ile Lys Ala
        435                 440                 445

Lys Ser Lys Lys Ile Pro Leu Gly Gly Ile Pro Ser Pro Ser Thr Gly
450                 455                 460

Ser Leu Val Pro Arg Gly Ser Cys Arg Ser Asn Ala Val Ala Glu Gln
465                 470                 475                 480

Gly Arg Lys Thr Gln Glu Phe Thr Gln Gln Ser Ala Gln Tyr Val Glu
                485                 490                 495

Ala Ala Arg Lys His Tyr Asp Ala Ala Glu Lys Leu Asn Ile Pro Asp
            500                 505                 510

Tyr Gln Glu Lys Glu Asp Ala Phe Met Gln Leu Val Pro Pro Ala Val
        515                 520                 525

Gly Ala Asp Ile Met Arg Leu Phe Pro Glu Lys Ser Ala Ala Leu Met
530                 535                 540

Tyr His Leu Gly Ala Asn Pro Glu Lys Ala Arg Gln Leu Leu Ala Met
545                 550                 555                 560

Asp Gly Gln Ser Ala Leu Ile Glu Leu Thr Arg Leu Ser Glu Arg Leu
                565                 570                 575

Thr Leu Lys Pro Arg Gly Lys Gln Ile Ser Ser Ala Pro His Ala Asp
            580                 585                 590

Gln Pro Ile Thr Gly Asp Val Ser Ala Ala Asn Lys Asp Ala Ile Arg
        595                 600                 605

Lys Gln Met Asp Ala Ala Ser Lys Gly Asp Val Glu Thr Tyr Arg
610                 615                 620

Lys Leu Lys Ala Lys Leu Lys Gly Ile Arg
625                 630

<210> SEQ ID NO 5
<211> LENGTH: 6
<212> TYPE: PRT
<213> ORGANISM: Artificial Sequence
<220> FEATURE:
<223> OTHER INFORMATION: Cyclic Peptide

<400> SEQUENCE: 5

Arg Ala Asp Asp Phe Cys
1               5
```